(12) United States Patent  (10) Patent No.: US 9,278,170 B2
Tennison et al.  (45) Date of Patent: Mar. 8, 2016

(54) CARBON AND ITS USE IN BLOOD CLEANSING APPLICATIONS

(75) Inventors: Stephen Robert Tennison, Surrey (GB); Oleksandr Prokopovyeh Kozynchenko, Hampshire (GB); Anthony Paul Rawlinson, Middlesex (GB); Gary James Phillips, Sussex (GB); Carol Angela Howell, West Sussex (GB); Susan Rachel Sandeman, East Sussex (GB); Sergey Victorovich Mikhalovsky, East Sussex (GB)

(73) Assignee: IMMUNTRIX THERAPEUTICS, INC., Rapid City, SD (US)

( * ) Notice: Subject to any disclaimer, the term of this patent is extended or adjusted under 35 U.S.C. 154(b) by 767 days.

(21) Appl. No.: 13/513,340

(22) PCT Filed: Dec. 9, 2010

(86) PCT No.: PCT/GB2010/052056
§ 371 (c)(1),
(2), (4) Date: Oct. 19, 2012

(87) PCT Pub. No.: WO2011/070363
PCT Pub. Date: Jun. 16, 2011

(65) Prior Publication Data
US 2013/0072845 A1  Mar. 21, 2013

(30) Foreign Application Priority Data
Dec. 9, 2009  (GB) .................................. 0921528.6

(51) Int. Cl.
*A61M 37/00* (2006.01)
*A61M 1/34* (2006.01)
*A61M 1/36* (2006.01)

(52) U.S. Cl.
CPC ............... *A61M 1/34* (2013.01); *A61M 1/3486* (2013.01); *A61M 1/362* (2014.02); *A61M 1/3496* (2013.01);
(Continued)

(58) Field of Classification Search
CPC ............... A61M 1/34; A61M 1/3486; A61M 2202/057; A61M 1/362; A61M 2202/07; A61M 2202/203; A61M 2202/0407
USPC .......... 604/5.04, 6.09, 6.11; 210/645, 500.27
See application file for complete search history.

(56) References Cited

U.S. PATENT DOCUMENTS 5,660,731 A  8/1997 Piechocki et al.
2006/0186044 A1*  8/2006 Nalesso ..................... 210/645
(Continued)

FOREIGN PATENT DOCUMENTS

DE  4331507 A1  4/1995
EP  0585016 A1  3/1994
(Continued)

OTHER PUBLICATIONS

Andrade, J. D.; Kunitomo, K.; Wagenen, Van R.; Kastigir, B.; Gough, D.; Kolff, W. J. Coated Adsorbents for direct blood perfusion: HEMA/activated carbon. American Society for Artificial Internal Organs: 17:1, 222-228, 1971.*
Mikhalovsky SV. Activated carbons in extracorporeal methods of medical treatment—time to reactivate the idea? Preprin.*
(Continued)

*Primary Examiner* — Leslie Deak
(74) *Attorney, Agent, or Firm* — Wick Phillips Gould & Martin, LLP; Jerry C. Harris, Jr.

(57) ABSTRACT

Whole blood is treated extracorporeally to remove substances contrary to health using mesoporous/microporous or macroporopus/microporous carbon in the form of beads or a channel monolith. The carbon may be the result of carbonizing a mesoporous or macroporous phenolic resin. Substances contrary to health include externally introduced toxins such as bacterially derived staphylococcus enterotoxins A, B, TSST-1 or autologous, biologically active molecules with harmful, systemic effects when their activity is excessive or unregulated. Examples include the removal of inappropriate amounts of pro- or anti-inflammatory molecules and toxic mediators of systemic inflammatory response syndrome related to sepsis, cardio-pulmonary by-pass surgery, ischaemic reperfusion injury; the removal of larger molecular weight and protein bound uremic toxins related to kidney and hepatic toxins related to liver failure and the removal of toxins relevant to biological and chemical warfare.

27 Claims, 14 Drawing Sheets

(52) U.S. Cl.
CPC .......... *A61M 2202/0057* (2013.01); *A61M 2202/0407* (2013.01); *A61M 2202/07* (2013.01); *A61M 2202/08* (2013.01); *A61M 2202/203* (2013.01)

(56) References Cited

U.S. PATENT DOCUMENTS

| | | | | |
|---|---|---|---|---|
| 2008/0223776 | A1* | 9/2008 | Sumian | A61M 1/3636 210/257.1 |
| 2011/0272343 | A1* | 11/2011 | Gourlay et al. | 210/493.1 |

FOREIGN PATENT DOCUMENTS

| | | |
|---|---|---|
| EP | 2072117 A1 | 6/2009 |
| EP | 2087916 A1 | 8/2009 |
| RU | 2199351 | 2/2003 |
| WO | WO-02/072240 A2 | 9/2002 |
| WO | WO-2005/099789 A1 | 10/2005 |
| WO | WO-2007/070455 A2 | 6/2007 |

OTHER PUBLICATIONS

Mikhalovsky SV. Emerging technologies in extracorporeal treatment: focus on adsorption Perfusion Jan. 2003 18: 47-54.*

British Application Serial No. GB0921528.6, Search Report mailed Jan. 25, 2011, 4 pgs.

International Application Serial No. PCT/GB2010/052056, International Search Report mailed Apr. 28, 2011, 4 pgs.

Sandeman, S. R., et al., "Inflammatory cytokine removal by an activated carbon device in a flowing system", *Biomaterials*, vol. 29, (2008), 1638-1644.

Tennison, S. R., "Phenolic-resin-derived activated carbons", *Applied Catalysis A: General*, 173, (1998), 289-311.

Yushin, G., et al., "Mesoporous carbide-derived carbon with porosity tuned for efficient adsorption of cytokines", *Biomaterials*, 27, (2006), 5755-5762.

International Application Serial No. PCT/GB2010/052056, International Preliminary Report on Patentability mailed Jun. 21, 2012, 8 pgs.

International Application Serial No. PCT/GB2010/052056, Written Opinion mailed Apr. 28, 2011, 6 pgs.

* cited by examiner

CARBON AND ITS USE IN BLOOD CLEANSING APPLICATIONS

RELATED APPLICATIONS

This application is a nationalization under 35 U.S.C. 371 of PCT/GB2010/052056, filed Dec. 9, 2010 and published as WO 2011/070363 A1 on Jun. 16, 2011, which claimed priority to United Kingdom Patent Application Serial No. 0921528.6, filed Dec. 9, 2009; which applications and publication are incorporated herein by reference in their entirety.

FIELD OF THE INVENTION

This invention relates to microporous/mesoporous or microporous/macroporous carbon and its use for the removal from blood of substances contrary to health. These include externally introduced toxins such as bacterially derived staphylococcus enterotoxins A, B, TSST-1 or autologous, biologically active molecules with harmful, systemic effects when their activity is excessive or unregulated. Examples include the removal of inappropriate amounts of pro- or anti-inflammatory molecules and toxic mediators of systemic inflammatory response syndrome related to sepsis, cardiopulmonary by-pass surgery, ischaemic reperfusion injury; the removal of larger molecular weight and protein bound uremic and liver toxins related to chronic kidney and liver failure respectively, the removal of toxins relevant to biological and chemical warfare.

BACKGROUND TO THE INVENTION

Purification of Blood in Dialysis Patients

End-stage renal failure (ESRF) is an increasingly prevalent and disproportionately costly condition. The majority of patients receiving renal replacement therapy (RRT) undergo haemodialysis (HD) which primarily removes small water soluble molecules. However, most protein bound and larger molecular weight uremic toxins remain in the body, impairing cardiovascular function and contributing to the morbidity and mortality of HD patients. ESRF maintains a high morbidity and mortality rate despite improved therapy options. A complex picture is emerging of the pathophysiology associated with CKD progression in which newly identified uremic toxins not removed by HD appear to play a central role. A clinically effective and cost efficient device could transform ESRF patient care. Uremic toxin retention in renal failure is a complex problem that cannot be adequately modelled by measuring simple markers like urea and creatinine Middle molecules and protein bound molecules are not very efficiently removed by current dialysis therapies and may be very important mediators of pathology associated with chronic kidney disease. The removal of currently "difficult to remove" uremic toxins may diminish complications, extending and greatly improving patient quality of life. No cost-effective and clinically efficient devices exist currently.

U.S. Pat. No. 4,169,051 Satoh is concerned with the use of activated carbon as an adsorbent for the purification of blood in dialysis patients. It discusses the use of crushed activated carbon of vegetable origin but mentions problems of carbon dust and platelet adhesion which are not overcome by coating. Furthermore the crushed activated carbon cannot adsorb materials of medium molecular weight e.g. so-called "kidney toxin". Molecular weight in this context is explained in U.S. Pat. No. 5,194,157 Ghezzi, "medium molecules" being defined as those of molecular weight 300-1500 D. Granular activated carbon was said to have superior properties with regard to dust but is poorly adsorbent. The proposed solution is to use beads of activated carbon derived from pitch and coated with a semi-permeable film-forming material selected from pyroxylin, polypropylene, vinyl chloride-vinylidene chloride copolymer, ethylene glycol polymethacrylate and collagen. In an embodiment, beads are formed from pitch softening at 205° C. which was melt-dispersed into water using benzene and aqueous polyvinyl alcohol as suspending agent to form beads which were heated in a fluidized bed to remove benzene, carbonised in nitrogen at 1000° C. and coated with pyroxylin. The resulting beads were said to be able to remove kidney toxin from blood and to exhibit only slight platelet adhesion, which could be avoided completely by coating with albumen.

U.S. Pat. No. 4,358,376 Moriuchi discloses a detoxifying column comprising non-coated particles of petroleum pitch which has been ultrasonically cleaned to remove dust.

U.S. Pat. No. 5,194,157 Ghezzi prefers to use vegetable-derived activated carbon in the form of microgranules which have "a multitude of minute channels opening in corresponding pores on its surface", a contact surface area of up to 1000 $m^2/g$ and adsorption spectrum of 100-20000 D, but to use that material only in relation to an ultrafiltrate from which blood corpuscles have been removed.

RU-C-2119351 Petrik discloses separation of plasma from blood and treatment of the plasma with expanded graphite and carbon nanotubes to remove uric acid and creatine.

US-A-2004/0141932 Umekawa et al. discloses a medical adsorbent comprising activated carbon obtained by carbonising and activating a spherical phenolic resin. However, only microporoisty is indentified and there is no disclosure or suggestion of incorporating mesoporosity into the resin. GB-A-2025385 Murakama et al. discloses a spherical active carbon made by suspension polymerization of styrene/divinylbenzene, treatment of the resulting polymer with $SO_3$ to make it infusible, followed by carbonisation and activation. Again there is no disclosure or suggestion to incorporate mesopores or active macropores, and the pores are stated to be substantially all of size<500 Å, preferably <200 Å so as to substantially avoid adsorption of high molecular weight materials such as blood serum protein.

Removing Inappropriate Amounts of Anti-Inflammatory Mediators

WO 2005/099789 Tennison, the disclosure of which is incorporated herein by reference, is concerned with the treatment of sepsis by removal of inappropriate amounts of pro or anti-inflammatory mediators e.g. IL-4, IL, 6, IL, 8, IL-10, IL-11, IL-13 and IL-1. It discloses passing blood through a monolithic porous carbon structure. Plasma components are allowed to pass through the walls of the monolith. Two streams are thereby formed: a plasma permeate stream that has passed through the walls of the monolith and a retentate stream containing the majority of the blood cells. Contrary substances are adsorbed in the walls of the monolith from the plasma permeate stream, after which the plasma permeate stream and the retentate stream are recombined. The monolithic porous carbon through which the blood plasma passes may have a mean pore size>500 nm and pores of size 2-500 nm within the carbon matrix for adsorption of middle and high molecular weight molecules. One embodiment of the monolith is tubular and another embodiment has rectangular channels of size 100-2000 µm, wall thickness 100-2000 µm and open area 30-60%. The monolithic porous structure may have a surface area of at least 600 $m^2/g$. It may be made by partially curing a phenolic resin to a solid, in embodiments of particle size 10-100 µm, comminuting the partially cured resin, extruding the comminuted resin to give a form-stable sintered product and carbonising and activating that product. Preferred products are derived from resin of powder size 20-75 μm which provides for a macropore size of 4-15 μm and a macropore volume of about 40%.

WO 2007/070455 Gogotsi explains that even advanced activated carbons exhibit only partial performance in adsorption of large inflammatory proteins, mostly due to a limited surface area accessible to the adsorbate. It discloses a carbon composition produced from a carbon-containing inorganic precursor e.g. a ternary carbide such as $Ti_2AlC$ or carbonitride which was said to have a large surface area accessible to cytokines e.g. TNF and IL-6.

Much of the complexity of the existing systems for removing inappropriate amounts of anti-inflammatory mediators or otherwise treating blood arises from the requirement to separate the blood cells from the plasma prior to treating the plasma due to the interaction of the adsorbents with the blood. There is a requirement therefore for an efficient and cost effective extracorporeal device which allows a stream of whole blood to be treated with an effective adsorbent system for the removal of the inflammatory molecules. For such a device to be effective it is also essential that the materials used do not cause a further immune response, excessive platelet activation (blood coagulation) on the adsorbent or haemolysis of the red blood cells.

SUMMARY OF THE INVENTION

We have shown that a novel, finely controlled multi-porous and surface structure activated carbon material can be used for the direct and effective removal of cytokines, uremic toxins, liver toxins and other biologically active molecules such as bacterial endotoxin and exotoxin from blood without prior separation of the blood into cells and plasma. This occurs with no detectable degradation of the blood cells and without any significant blocking of the carbon surface due to platelet adhesion. Other adverse effects including haemolysis, cytotoxicity, activation of white blood cells leading to an inflammatory cascade have not been noted. Treatment of plasma cannot be equated with treatment of whole blood since the possibility of adverse effects on the blood cells cannot be ignored. The carbon may be uncoated so that the range of pores within it are available for adsorption of contrary substances, whereas coated carbons have no or limited capacity to adsorb middle and larger molecular weight proteins.

The invention provides a method for extracorporeal treatment of whole blood to remove contrary substances described herein and provide treated blood returnable to the body, which method comprises contacting the blood with microporous/mesoporous or microporous/macroporous carbon.

The blood may be from a patient with end-stage renal failure who is receiving hemodialysis (HD), that does not remove protein bound and larger molecular weight uremic toxins which remain in the body, impairing cardiovascular function and contributing to the morbidity and mortality of patients. The carbon provides an effective sorbent adjunct to augment HD wherein the incoming stream from the patient is cleaned of remaining uremic toxins with the treated blood for return to the bloodstream of the patient.

The blood may alternatively be from a patient with liver failure, where build-up of hepatic toxins can result in conditions such as Hepatic encephalopathy and jaundice caused by increased levels of bilirubin. The carbon provides an effective sorbent to remove the build-up of hepatic toxins in acute or acute-on-chronic liver failure, wherein the incoming stream from the patient is cleansed of hepatic toxins with the treated blood for return to the bloodstream of the patient.

The invention uses in some embodiments a highly porous, multi-modal, synthetic pyrolysed carbon for use as an adsorbent blood filtration module to augment HD and for other blood purification applications. Bimodal micro/meso and micro/macro porous carbon materials have been developed for direct contact with blood. The carbons are haemocompatible (Assessing the in vitro biocompatibility of a novel device for the treatment of sepsis, *Biomaterials*, 23(205) 7124 Sandeman et al) and can remove middle molecular weight inflammatory cytokines and bacterial toxins implicated in the progression of sepsis and other systemic inflammatory conditions and in a size range suggesting suitability additionally for removal of the larger molecular weight and protein bound uremic and liver toxins. The present carbons in bead and monolith form have been shown to remove protein bound uremic toxins from human plasma. The present carbon beads have been shown to remove the protein bound liver toxin bilirubin from human plasma. The tailored porosity of the carbons and superior surface area available for adsorption permits removal of key protein bound and larger uremic toxins not removed by current RRT.

According to the invention there is provided a method for the treatment of blood which comprises passing the blood through either a bed of the controlled structure carbon in bead form where the bed can comprise either a packed bed of the beads, or the beads immobilised in a porous polymeric carrier or through an open monolithic structure where the blood passes along the channels of the monolith.

The latter channel structure has the benefit of a low pressure drop but is less effective in the adsorption of the macromolecules due to the hydrodynamic characteristics of the channel structure. Nonetheless satisfactory removal can still be achieved by continuous recycle of the blood from the patient, through the device and back to the patient.

By contrast the use of small beads of the carbon, as are required to achieve good adsorption kinetics, may lead to an excessive pressure drop across a simple packed bed and it may be desirable then to disperse the beads into, for instance, a fibrous polymeric matrix. Such systems are well known for the production of encapsulated filters for air purification in clean rooms and also for the production of chemical defence suiting materials (WO 2010/082064 A2) incorporated herein by reference.

A haemoperfusion renal assist device may be provided that could run in line with current dialysis membranes, consisting of a haemocompatible medical grade carbon monolith with a pore structure tailored to remove middle molecules and protein bound uremic toxins, or with a similar removal; system based on small carbon beads, and may provide toxin removal and may result in improved patient outcome, an enhanced quality of life, and a reduction in complications associated with CKD. In this regard the ability to remove both small molecules and larger molecules via the mesoporous or active microporous structure of the carbon may be of assistance.

BRIEF DESCRIPTION OF THE DRAWINGS

How the invention may be put into effect will now be described, by way of example only, with reference to the accompanying drawings, in which.

DETAILED DESCRIPTION OF PREFERRED EMBODIMENTS

Figure 1:
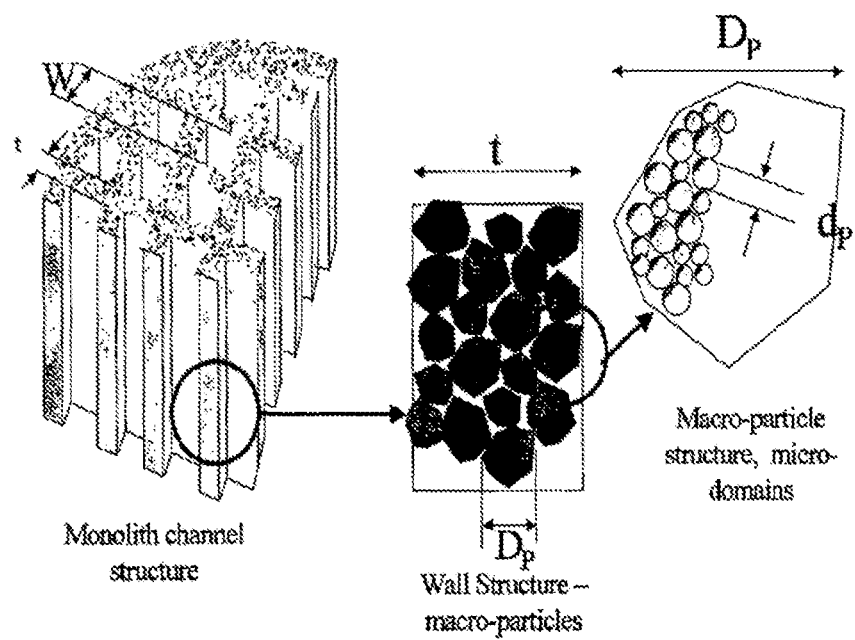
FIG. 1 is a trimetric view of a monolith showing a longitudinal channel structure thereof, accompanying detail views showing macroparticles forming the wall structure of the monolith and micro-domains of an individual particle.

Whole blood may be treated extracorporeally to remove substances contrary to health using mesoporous/microporous or macroporous/microporous carbon in the form of beads or a channel monolith. The carbon may be the result of carbonising a mesoporous or macroporous phenolic resin. The contrary substances include externally introduced toxins such as bacterially derived staphylococcal enterotoxins A, B, TSST-1 or autologous, biologically active molecules with harmful, systemic effects when their activity is excessive or unregulated. Examples include the removal of inappropriate amounts of pro- or anti-inflammatory molecules and toxic mediators of systemic inflammatory response syndrome related to sepsis, cardio-pulmonary by-pass surgery, ischaemic reperfusion injury; the removal of larger molecular weight and protein bound uremic toxins related to chronic kidney and liver failure; the removal of toxins relevant to biological and chemical warfare.

Contrary Substances

The contrary substances which can be removed from the blood include:

free water soluble low mol weight solutes (<500 D) eg creatinine, urea, ADMA (asymmetrical dimethylarginine);

protein bound solutes eg leptin peptide, p-cresol sulphate, indoxyl sulphate, AGE (advanced glycation end products);

middle MW and large molecules (MW>500 D) including bacterial endotoxins e.g. Lipopolysaccharide (LPS); exotoxins e.g. *Staphylococcal aureus* entertotoxin A (SEA), *Staphylococcal aureus* entertotoxin B (SEB), toxic shock syndrome toxin 1 (TSST-1)); cytokines; circulating pro and anti-inflammatory mediators e.g. IL-1β, IL-4, IL-6, IL-8, IL-10, IL-11, IL-13, and TNF.

Preparation of Porous Carbon from Phenolic Resin

The applicants have developed a number of processes for the production of activated carbon containing micro-, meso- and macropores from porous phenolic resins, the products commonly taking the form of beads or monoliths, and much of this technology is applicable in the present invention.

As used herein, the term "micropore" refers to a pores with diameter<2 nm, as measured by nitrogen adsorption and mercury porosimetry methods and as defined by IUPAC.

As used herein, the term "mesopore" refers to pores with diameter from ca. 2 nm to ca. 50 nm, as measured by nitrogen adsorption and mercury porosimetry methods and as defined by IUPAC.

As used herein, the term "macropore" refers to pores with diameters larger than 50 nm, as measured by nitrogen adsorption and mercury porosimetry methods and as defined by IUPAC. In relation to this invention there are two types of macropores. In macroporous beads they are located within beads and formed by pore-formers. Their size is 50-500 nm, typically 70-200 nm. These macropores are very effective in adsorption of cytokines. In simple monoliths there are macropores present that are formed due to the voids between sintered particles. Their size is typically 700-2000 nm. These macropores do not work for cytokines adsorption and that is why monoliths with more complex pore structures comprising micropores, small macropores and large macropores have had to be created.

The evidence from the trial work applicants have carried out has demonstrated that relatively large mesopores or active macropores are needed to provide for the adsorption of cytokines and the other contrary substances of interest. Typically a precursor resin formulation is used which comprises a large proportion of pore former, e.g. 250 parts ethylene glycol or other pore former to 100 parts of resin-forming components WO 02/12380 (Tennison et al., the disclosure of which is incorporated herein by reference) discloses making a mesoporous resin by condensing a nucleophilic component which comprises a phenolic compound or a phenol condensation prepolymer with at least one electrophilic cross-linking agent selected from formaldehyde, paraformaldehyde, furfural and hexamethylene tetramine in the presence of a pore-former selected from the group consisting of a diol (e.g. ethylene glycol), a diol ether, a cyclic ester, a substituted cyclic ester, a substituted linear amide, a substituted cyclic amide, an amino alcohol and a mixture of any of the above with water to form a resin. The pore-former is present in an amount effective to impart meso- or macroporosity to the resin (e.g. at least 120 parts by weight of the pore former being used to dissolve 100 parts by weight of the total resin forming components, i.e. nucleophilic component plus electrophilic component), and it is removed from the porous resin after condensation by cascade washing with water or by vacuum drying. The resulting resin may be carbonised by heating in an inert atmosphere to a temperature of at least 600° C. to give a material having a bimodal distribution of pores, the pore structure as estimated by nitrogen adsorption porosimetry comprising micropores and mesopores or macropores. The value for the differential of pore volume with respect to the logarithm of pore radius (dV/d log R) for the mesopores is greater than 0.2 for at least some values of pore size in the range 20-500 Å. The mesoporous carbon may have a BET surface area of 250-800 m$^2$/g without activation. It may be activated by heating it at high temperature in the presence of carbon dioxide, steam or a mixture thereof, e.g. by heating it in carbon dioxide at above 800° C., or it may be activated by heating it in air at above 400° C. It may then have surface areas of up to 2000 m$^2$/g and even higher e.g. 1000-2000 m$^2$/g. As used herein the term "BET surface area" is determined by the Brunauer, Emmett, and Teller (BET) method according to ASTM D1993-91, see also ASTM D6556-04.

Phenolic Resins—Nucleophilic Component

Resins for making carbonaceous material can be prepared from any of the starting materials disclosed in WO 02/12380. Nucleophilic components may comprise phenol, bisphenol A, alkyl phenols e.g. cresol, diphenols e.g. resorcinol and hydroquinione and aminophenols e.g. m-amino-phenol.

It is preferred to use as nucleophilic component a phenolic novolac or other similar oligomeric starting material which because it is already partly polymerized makes polymerization to the desired resin a less exothermic and hence more controllable reaction. The preferred novolacs have average molecular weights (AMW) in the range of from 300 to 3000 prior to cross-linking (corresponding to a DP with respect to phenol of about 3-30). Where novolac resins are used, they may be solids with melting points in the region of 100° C. Novolac resins of AMW less than 2000 and preferably less than 1500 form resins which on carbonisation tend to produce carbons with desired pore size distributions using lower amounts of pore former. Novolacs are thermally stable in that they can be heated so that they become molten and cooled so that they solidify repeatedly without structural change. They are cured on addition of cross-linking agents and heating. Fully cured resins are infusible and insoluble.

Whilst commercial novolacs are largely produced using phenol and formaldehyde, a variety of modifying reagents can be used at the pre-polymer formation stage to introduce a range of different oxygen and nitrogen functionalities and cross-linking sites. These include but are not limited to:

(a) Dihydric phenols e.g. resorcinol and hydroquinone. Both are more reactive than phenol and can lead to some cross-linking at the pre-polymer production stage. It is also possible to introduce these compounds at the cross-linking stage to provide different cross-linking paths. These also increase the oxygen functionality of the resins.

(b) Nitrogen containing compounds that are active in polycondensation reactions, such as urea, aromatic (aniline, m-amino phenol) and heteroaromatic (melamine) amines. These allow the introduction of specific types of nitrogen functionality into the initial polymer and final carbon and influence the development of the mesoporous structure of both the resins and the final carbons. Like hydroquinone and resorcinol, all the nitrogen containing nucleophilic modifying reagents which can be used possess two or more active sites and are more reactive in condensation reactions than phenol or novolacs. It means that they are first to react with primary cross-linking agents forming secondary cross-linking agents in situ.

The nucleophilic component may be provided alone or in association with a polymerization catalyst which may be a weak organic acid miscible with the novolac and/or soluble in the pore former e.g. salicylic acid, oxalic acid or phthalic acid.

The concentration of novolac in the pore former may be such that when combined with the solution of cross-linking agent in the same pore former the overall weight ratio of pore former to (novolac+cross-linking agent) is at least 125:100 by weight. The actual ratios of novolac:pore former and cross-linking agent:pore former are set according to convenience in operation e.g. in the case of the process disclosed in WO 2008/043983 (Tennison) by the operational requirements of a bead production plant and are controlled by the viscosity of the novolac:pore former solution such that it remains pumpable and by the ratio of cross-linking agent:pore former such that the cross-linking agent remains in solution throughout the plant.

Cross-Linking Agents for Phenolic Resins

The cross-linking agent is normally used in an amount of from 5 to 40 parts by weight (pbw) per 100 parts by weight of the nucleophilic components e.g. novolac. It may be, for example, an aldehyde e.g. formaldehyde or furfural, it could be hexamethylenetetramine (hexamine), or hydroxymethylated melamine.

Hexamine is preferably used as cross-linking agent. In embodiments requiring a completely cured resin, it is preferably used for cross-linking novolac resin at a proportion of 10 to 25 pbw e.g. about 15 to 20 pbw hexamine per 100 pbw of novolac. This ensures formation of the solid resin with maximal cross-linking degree and ensures the stability of the mesopore structure during subsequent removal of the pore former.

Pore-Formers

The pore former also acts as solvent. Thus, the pore former is preferably used in sufficient quantities to dissolve the components of the resin system, the weight ratio of pore former to the total components of the resin system resin being preferably at least 1.25:1.

Details of suitable pore formers are given in WO 02/12380 (Tennison). The pore former may be, for example, a diol, a diol-ether, a cyclic ester, a substituted cyclic or linear amide or an amino alcohol e.g. ethylene glycol, 1,4-butylene glycol, diethylene glycol, triethylene glycol, γ-butyrolactone, propylene carbonate, dimethylformamide, N-methyl-2-pyrrolidinone and monoethanolamine, ethylene glycol being preferred, and where the selection is also limited by the thermal properties of the solvent as it should not boil or have an excessive vapour pressure at the temperatures used in the curing process.

It is thought that the mechanism of meso- and macropore generation is due to a phase separation process that occurs during the cross-linking reaction. In the absence of a pore former, as the linear chains of pre-polymer undergo cross-linking, their molecular weight initially increases. Residual low molecular weight components become insoluble in the higher molecular weight regions causing a phase separation into cross-linked high molecular weight domains within the lower molecular weight continuous phase. Further condensation of light components to the outside of the growing domains occurs until the cross-linked phase becomes essentially continuous with residual lighter pre-polymer trapped between the domains. In the presence of a low level of pore former the pore former is compatible with, and remains within, the cross-linked resin domains, (e.g., <120 parts/100 parts Novolac for the Novolac-Hexamine-Ethylene Glycol reaction system), whilst the remainder forms a solution with the partially cross-linked polymer between the domains. In the presence of higher levels of pore former, which exceed the capacity of the cross-linked resin, the pore former adds to the light polymer fraction increasing the volume of material in the voids between the domains that gives rise to the mesoporosity and/or macroporosity. In general, the higher the pore former content, the wider the mesopores, up to macropores, and the higher the pore volume.

This phase separation mechanism provides a variety of ways of controlling the pore development in the cross-linked resin structures. These include chemical composition and concentration of the pore former; chemical composition and quantity of the cross-linking electrophilic agents, presence, chemical nature and concentration of modifying nucleophilic agents, chemical composition of phenolic nucleophilic components (phenol, novolac), the presence of water within the solvent and concentration of any curing catalyst if present.

Production of Resin Precursor and Carbon in Bead Form

In WO 02/12380, production of the resin in both powder and bead form is disclosed. Production of the bead form may be by pouring a solution of a partially cross-linked pre-polymer into a hot liquid such as mineral oil containing a dispersing agent and stirring the mixture. The pre-polymer solution forms into beads which are initially liquid and then, as curing proceeds, become solid. The average bead particle size is controlled by several process parameters including the stirrer type and speed, the oil temperature and viscosity, the pre-polymer solution viscosity and volume ratio of the solution to the oil and the mean size can be adjusted between 5 and 2000 µm, although in practice the larger bead sizes are difficult to achieve owing to problems with the beads in the stirred dispersion vessel. The beads can then be filtered off from the oil. In a preparative example, industrial novolac resin is mixed with ethylene glycol at an elevated temperature, mixed with hexamine and heated to give a viscous solution which is poured into mineral oil containing a drying oil, after which the mixture is further heated to effect curing. On completion of curing, the reaction mixture is cooled, after which the resulting porous resin is filtered off, and washed with hot water to remove pore former and a small amount of low molecular weight polymer. The cured beads are carbonized to porous carbon beads which have a pore structure as indicated above, and may be activated as indicated above. It is stated that the beads can be produced with a narrow particle size distribution e.g. with a D90.D10 of better than 10 and preferably better than 5. However, the bead size distribution that can be achieved in practice in stirred tank reactors is relatively wide, and the more the process is scaled up the worse the homogeneity of the mixing regime and hence the particle size distribution becomes wider.

WO 2008/043983 (Tennison) describes and claims a process for producing discrete solid beads of polymeric material e.g. phenolic resin having a porous structure, which process may produce resin beads on an industrial scale without aggregates of resin building up speedily and interrupting production. The process comprises the steps of: (a) combining a stream of a polymerizable liquid precursor e.g. a novolac and hexamine as cross-linking agent dissolved in a first polar organic liquid e.g. ethylene glycol with a stream of a liquid suspension medium which is a second non-polar organic liquid with which the liquid precursor is substantially or completely immiscible e.g. transformer oil containing a drying oil; (b) mixing the combined stream to disperse the polymerizable liquid precursor as droplets in the suspension medium e.g. using an in-line static mixer; (c) allowing the droplets to polymerise in a laminar flow of the suspension medium so as to form discrete solid beads that cannot agglomerate; and (d) recovering the beads from the suspension medium.

Dispersion Medium

For bead production, the pore former comprises a polar organic liquid e.g. ethylene glycol chosen in combination with dispersion medium which is a non-polar organic liquid so as to form a mainly or wholly immiscible combination, the greater the incompatibility between the pore former which forms the dispersed phase and the dispersion medium, the less pore former becomes extracted into the dispersion medium. The pore former desirably has a greater density than the dispersion medium with which it is intended to be used so that droplets of the pore former containing dissolved resin-forming components will pass down a column more rapidly than a descending flow of dispersion medium therein. Both protic and aprotic solvents of different classes of organic compounds match these requirements and can be used as pore formers, both individually and in mixtures. In addition to dissolving the reactive components and any catalyst, the pore former should also, in the case of phenolic resins, be compatible with water and/or other minor condensation products (e.g. ammonia) which are formed by elimination as polymerization proceeds, and the pore former is preferably highly miscible with water so that it can be readily removed from the polymerized resin beads by washing.

The dispersion medium is a liquid which can be heated to the temperature at which curing is carried out e.g. to 160° C. without boiling at ambient pressure and without decomposition and which is immiscible with ethylene glycol and with the dissolved components therein. It may be hydrocarbon-based transformer oil which is a refined mineral oil and is a by-product of the distillation of petroleum. It may be composed principally of $C_{15}$-$C_{40}$ alkanes and cycloalkanes, have a density of 0.8-0.9 depending upon grade and have a boiling point at ambient pressure of 260-330° C., also depending upon grade. Transformer oil has a viscosity of about 0.5 poise at 150° C. which is a typical cure temperature. Transformer oil or other dispersion medium may be used in volumes 3-10 times the volume of the combined streams of nucleophilic precursor and crosslinking agent e.g. about 5 times.

Dispersing Agents

Preferred dispersing agents which are dissolved in the dispersion medium before that medium is contacted with the reaction mixture to be dispersed therein to retard droplet coalescence are either sold as drying oils e.g. Danish oil or are produced by partially oxidizing naturally occurring precursors such as tung oil, linseed oil etc. The dispersing agents are consumed as the process proceeds, so that if the dispersion medium is recycled, dispersing agent in the recycled oil stream should be replenished. The dispersing agent is conveniently supplied as a stream in solution in the dispersion medium e.g. transformer oil and e.g. in an amount of 5-10% v/v where Danish oil is used which contains a low concentration of the active component to give final concentration of the dispersant in the dispersion medium 0.2-1% v/v. Higher dispersant concentrations would be used in the case of oxidised vegetable oils.

Post-Treatment of Resin Beads

The resin beads formed as described above may be carbonised and optionally activated. In WO 2008/043982 (Tennison, the disclosure of which is incorporated herein by reference) there is provided a process for carbonizing and activating carbonaceous material and especially the solid beads of polymeric material resulting from the process of WO 2008/043983, which comprises supplying the material to an externally fired rotary kiln maintained at carbonizing and activating temperatures, the kiln having a downward slope to progress the material as it rotates, the kiln having an atmosphere substantially free of oxygen provided by a countercurrent of steam or carbon dioxide, and annular weirs being provided at intervals along the kiln to control progress of the material.

Production of Resin Precursor and Carbon in Monolithic Form

By "monolithic" is meant that the porous carbon is in a single piece i.e. not granular or not composed of granular carbons bound together by a binder etc. The monolithic carbon contains large transport channels. For a symmetrical monolith (FIG. 1) a continuous channel structure is defined by a channel dimension, W, and a wall thickness, t, or for an asymmetric monolith by channel length and width or other relevant dimensions as well as wall thickness t. These fix the ratio of open to closed area and therefore the flow velocity along the channels of the monolith. The walls of the monolithic carbon have a macroporous structure providing continuous voids or pores generated by the voids between the resin particles as shown in FIG. 1.

Known methods for the production of complex shaped controlled porosity adsorbent material are discussed in WO 2004/087612 (Blackburn and Tennison, the disclosure of which is incorporated herein by reference). The inventors explain that there are very few viable routes for the production of complex shaped controlled porosity adsorbent materials. For instance, they explain that activated carbon is traditionally produced by taking a char, made by pyrolysing an organic precursor or coal, grinding the char to a fine powder, mixing this with a binder, typically pitch, and extruding or pressing to give a "green" body. The green body is then further fired to pyrolyse the binder and this is then typically further activated in steam, air, carbon dioxide or mixtures of these gases to give the high surface activated carbon product. The drawback to this route is that the binder, which is usually a thermoplastic material, goes through a melting transition prior to pyrolytic decomposition. At this point the material is weak and unable to support a complex form. This, combined with the problems of activating the fired body, limits the size and shape of the products to typically simple extrudates. An alternative route is to take an activated carbon powder and form this directly into the final shape. In this instance a range of polymeric binders have been used that remain in the final product. The main drawback to this route is that high levels of binders are required and these then tend to both fill the pores of the activated carbon powder and encapsulate the powder leading to a marked reduction in adsorption capacity and deterioration in the adsorption kinetics. The presence of the polymeric phase also degrades the physical and chemical stability of the formed material, severely limiting the range of applicability. A further alternative is to take a formed ceramic material, such as a multichannel monolith, and to coat this with a carbon forming precursor such as a phenolic resin; this can then be fired and activated to produce a ceramic-carbon composite. The main limitations of this route are the cost associated with the ceramic substrate and the relatively low volume loading of carbon. At high degrees of activation it is possible to produce a mesoporous carbon although the carbon volumetric loading and the mechanical stability of the carbon is further reduced.

In embodiments carbonised and optionally activated monoliths are now formed from phenolic resin precursors. Monolithic porous carbon can be made by partially curing a phenolic resin to a solid, comminuting the partially cured resin, forming the comminuted particles into a dough by the addition of water and extrusion agents such as Methocell™, and extruding the dough to form a resin monolith. Provided that the cure of the resin was carried out correctly the resin particles sinter without the application of heat so as to produce a form-stable sintered resin product and then the form-stable sintered product is carbonised and activated. EP 0 254 551 gives details of methods of production of the porous resins suitable for forming the porous carbon used in the present invention and its contents are included herein by reference. WO 02/072240 (Place et al. the disclosure of which is incorporated herein by reference) gives details of producing monolithic structures using the sintered resin structures of EP-A-0254551.

In the standard process, the resin cure is controlled so that it is sufficient to prevent the resin melting during subsequent carbonisation but low enough that the particles produced during the milling step can sinter during subsequent processing. The temperature and duration of the partial curing step are selected as to give a degree of cure sufficient to give a sinterable product, and such that a sample of the partially cured solid when ground to produce particles in the size range 106-250 µm and tabletted in a tabletting machine gives a pellet with a crush strength which is not less than 1 N/mm. Preferably the pellet after carbonisation has a crush strength of not less than 8 N/mm.

By "sintering" we mean a step which causes the individual particles of phenolic resin to adhere together without the need for a separately introduced binder, while retaining their individual identity to a substantial extent on heating to carbonisation temperatures. Thus the particles must not melt after forming so as to produce a molten mass of resin, as this would eliminate the internal open porosity of the article. The open porosity (as opposed to the closed cells found in certain types of polymer foams) is believed to be important in enabling formed particles to retain their shape on carbonisation.

In one embodiment the comminuted resin particles have a particle size of 1-250 µm, more preferably 10-70 µm. Preferably the resin powder size is 20-50 µm which provides for a macropore size of 4-10 µm with a macropore volume of around 40%. The size of the particles is selected to provide a balance between diffusivity through the interparticle voids and within the particles.

As disclosed in WO 02/072240 the milled powder can then be extruded to produce polymeric monolithic structures with a wide range of cell structures, limited only by the ability to produce the required extrusion die and suitable dies are available commercially. At this stage the monolith has a bimodal structure—the visible channel structure with either the central channel in a simple tube or the open cells in a square channel monolith of 100-1000 µm cell dimension and cell walls with thickness 100-1000 µm and the macropore structure within the walls generated by the sintered resin particles.

The carbonisation steps take place preferably by heating above 600° C. for the requisite time e.g. 1 to 48 hours and takes place under an inert atmosphere or vacuum to prevent oxidation of the carbon. On carbonisation the material loses about 50% weight and shrinks by about 65% volume but, provided the resin cure stage was correctly carried out, this shrinkage is accommodated with no distortion of the monolith leading to a physical structure identical to that of the resin precursor but with dimensions reduced by ~30%. The macropore size is also reduced by ~30% although the macropore volume (ml/ml) remains unaltered. During carbonisation the microporosity of the porous carbon develops. After carbonisation there may be partial blocking of the micropores by the decomposition products from the carbonisation process. These blockages may be removed by activation to provide rapid access to the internal structure of the carbon that is essential for the operation of the monoliths as adsorption devices.

In the production of the resin in bead form there is as previously explained used a significant excess of the hexamine curing agent, to provide for fast and complete cross linking, to stabilise the mesopore structure which otherwise has a tendency to collapse.

Standard monoliths of carbon produced from phenolic resins by existing processes have a microporous/macroporous structure and introduction of mesoporosity is not intended. Forming monoliths having mesoporosity intentionally introduced into their structure gives rise to a number of difficulties. As previously described, an embodiment of a standard monolith production process comprises the steps of (i) pouring a mixture of novolak, cross-linking agent (hexamine) and pore former (ethylene glycol) into a tray, (ii) partially curing e.g. at 150° C. in an oven, (iii) crushing or hammer milling the cured resin to reduce its particle size, (iv) removing residual pore former by water washing or by vacuum drying, (v) jet milling the washed and dried material, (vi) extruding the material as a dough to form a resin monolith which is stabilised by sintering, and (vii) subjecting the sintered monolith to carbonization and activation.

It is necessary for the above process that the partially cured resin should be in a sinterable state, and that requirement limits the amount of cross-linking agent that can be used. The standard process used by the applicants for making micro/macroporous monolithic carbon from phenolic resins uses 5 parts by weight of hexamine as cross-linking agent, but if the same amount is used in the production sequence indicated above the induced mesoporosity collapses during pore former removal. It is therefore desirable to increase the proportion of cross-linking agent to an amount sufficient to stabilise the mesoporous structure but less than an amount that prevents the partially cured resin from sintering. Surprisingly we have now found that whilst the use of severely cured (16-20 parts hexmine) non-porous resin particles leads to the formation of monolithic structures with very poor properties, if the mesoporous resins are used it is possible to produce monoliths with reduced but still acceptable physical strength. Accordingly the monoliths of the current invention have been produced with 16 or 20 parts hexamine along with mesoporous resin produced with at least 150 parts ethylene glycol to 100 parts resin in the block cure process described above.

The walls of the monolithic carbon have a macroporous structure. By "macroporous" is meant that the carbon has continuous voids or pores. The macropore structure in the walls of a monolith is controlled by the particles used to form the monolith. When the monolith is made from macro-particles with a mean particle size of $D_P$ the macro pore size is typically 20% of the size of the precursor resin particles. This can be varied over a wide range from a maximum particle size of approximately 10% of the wall thickness, t, to a minimum practical particle size of about 10 μm. This gives a macropore size of 2-20 μm within the wall for a 1 mm wall thickness. The pore size fixes the diffusivity of the adsorbate molecules within the matrix. In embodiments the monoliths are square channel monoliths with a cell structure (cells per square cm) where the channel size is between 100 and 2000 μm and the wall thickness is between 100 and 2000 μm and with an open area of between 30 and 60% to give a good carbon packing density per unit volume and acceptable mass transfer characteristics.

Activated carbon materials for blood filtration in the present patent application have been prepared by the generic methods described below though they may be prepared also by numerous variations of this method according to WO 02/12380 and WO 2008/043983. Alternatively mesoporous or macroporous resin-precursors for carbons may be prepared in blocks, then crushed, washed with water or vacuum-dried from ethylene glycol and further processed into monoliths.

The following examples illustrate a number of experiments conducted using whole blood and further experiments using plasma. In this application, the plasma experiments are used to model the ability of certain carbons to remove materials from whole blood.

Examples 1-3

Preparation of Beads of Porous Phenolic Resins and Corresponding Carbons

A solution of 100 parts by weight of industrial Novolac resin with an average molecular weight 700-800 D (Hexion Specialty Chemicals) in ethylene glycol was heated to 90-95° C. and thoroughly mixed for 2-5 minutes with a solution of 15-20 parts by weight of hexamethylenetetramine (hexamine) in ethylene glycol heated to the same temperature. The resulting clear solution was poured in a stream into 2.5-6 fold volume of stirred hot (150-155° C.) low viscosity mineral oil (insulating oil or transformer oil) containing 0.2-1% (v/v) of a dispersing agent which was an industrial drying oil (Danish oil), a major component being polyunsaturated (oxidised) vegetable oils. The temperature of the mixture fell to 135-140° C., and the mixture was reheated to 150-155° C. over a period of 15-20 minutes. Typically curing occurred within 1-2 minutes at around 140° C. followed by substantial evolution of gas, predominantly ammonia. The further heating to 150-155° C. for 15-20 minutes ensured the completion of curing. The mixture was cooled and the resulting beads were separated from the oil by filtration or centrifugation Ethylene glycol was removed from the resin either by multiple hot water extraction or by drying in vacuum (120° C. at 50 mm Hg). In the above procedure, compared to Example 3 of WO 02/12380, the hexamine content has been increased to 15-20 pbw per 100 pbw of novolac from the previously exemplified 9 pbw, and the temperature of the oil into which the resin solution is poured is increased from 115-120° C. to 150-155° C., and "flash" cure is brought about rather than a "slow" cure as previously exemplified.

Water-washed wet, dried or vacuum-dried resin beads were heat treated to produce carbon materials. A typical procedure comprised but is not restricted to carbonisation in a flow of carbon dioxide with temperature ramping from ambient to 800° C. at 3° C./min, classification by particle size and further "physical" activation of selected fraction in carbon dioxide flow at 900° C. Many variations of this routine known in the art may also be applied.

Figure 2A:
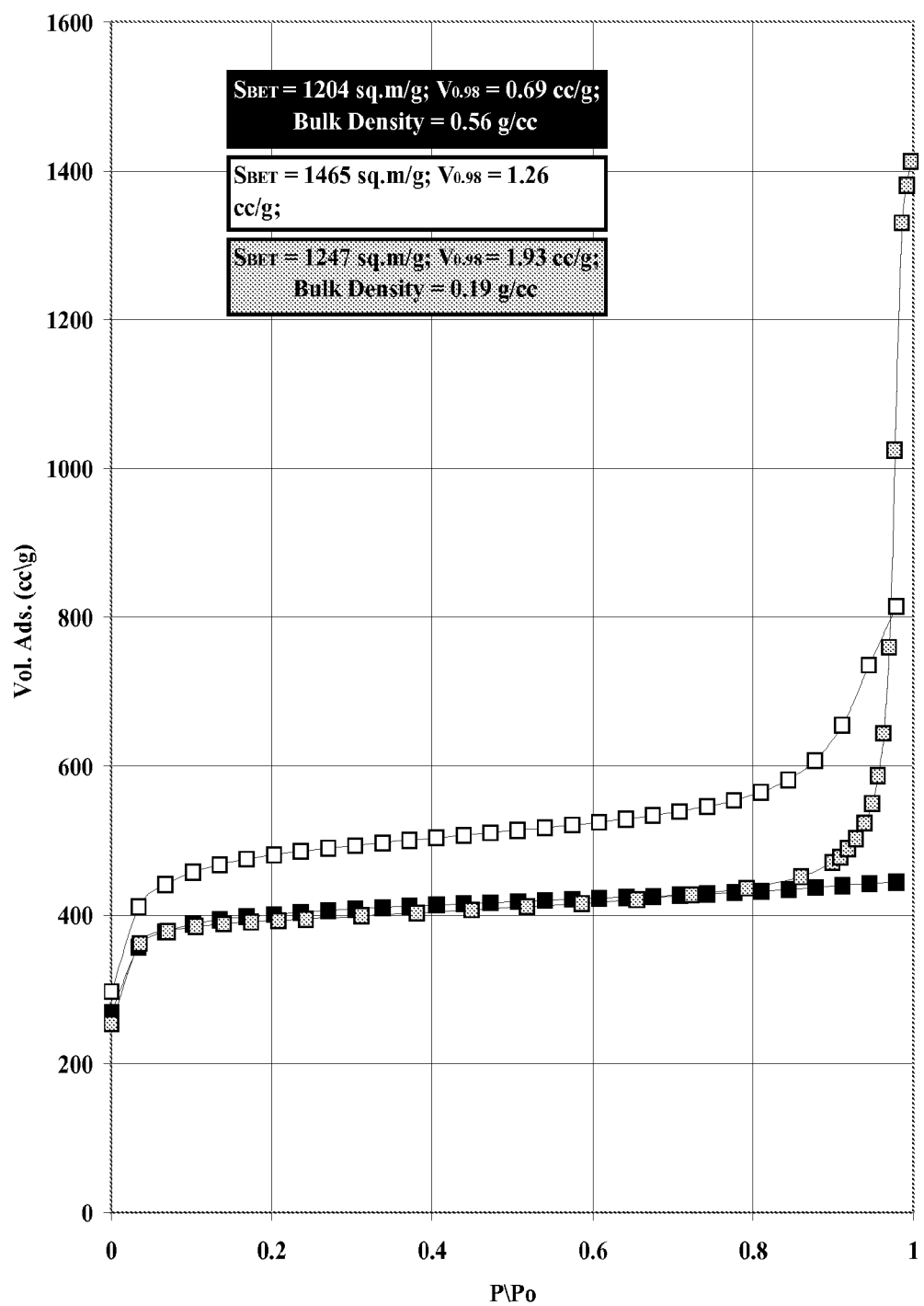
FIG. 2 shows nitrogen adsorption isotherms (a) and calculated pore size distributions (b) (BJH model) of activated carbons.
Figure 2B:
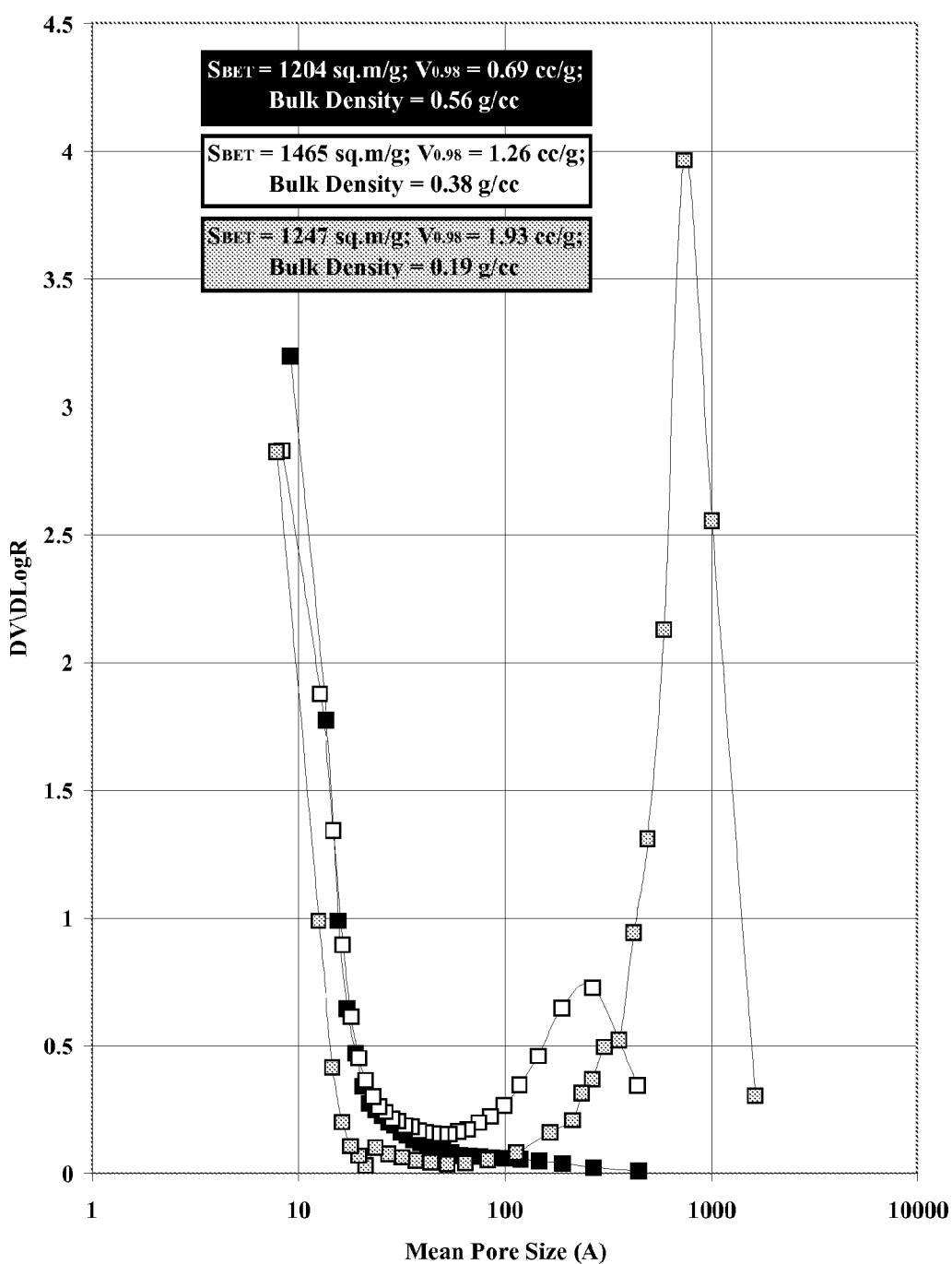

Pore size distribution in the resulting carbons is pre-determined by the porosity of the resin-precursor, which is controlled by the content of the solvent/pore former (typically but not restricted to ethylene glycol) in the resin composition. Table 1 below gives details of three resins compositions that are precursors to micro-, meso- and macro-porous carbons, as illustrated by nitrogen adsorption tests of activated materials used in adsorption studies (up to ~40% of activation burn-off in carbon dioxide) (FIGS. 2a and 2b).

The particle size distribution of resulting resin beads depends on various parameters including but not restricted to the type of stirring tool, stirring rate, viscosity of the resin solution, concentration of the dispersing agent, resin solution to oil ratio and temperature of the dispersion. Though the distribution is typically broad the size of the predominant fraction could effectively be shifted between ~10 micron and ~1 mm.

TABLE 1

| Example N | Novolac solution | | Hexamine solution | |
| --- | --- | --- | --- | --- |
| | Novolac | Ethylene Glycol | Hexamine | Ethylene Glycol |
| 1(micro) | 100 pbw | 40 pbw | 20 pbw | 80 pbw |
| 2(meso) | 100 pbw | 60 pbw | 20 pbw | 120 pbw |
| 3(macro) | 100 pbw | 100 pbw | 20 pbw | 150 pbw |

FIG. 2 shows nitrogen adsorption isotherms (a) and calculated pore size distributions (BJH model) (b) of activated carbons derived from the resins of examples 1, 2 and 3 respectively (compositions from Table 1):
microporous (black squares);
mesoporous (blank squares) and
macroporous (grey squares).

Example 4

Preparation of Carbon Monoliths

A hot solution of 100 parts by weight of Novolac resin in 100 w.p. of ethylene glycol was thoroughly mixed with a hot solution of 16 parts by weight of hexamine in 190 parts by weight of ethylene glycol. The resulting solution was transferred into a stainless steel tray, covered with a lid and placed into flameproof oven. Raising the temperature to 150° C. and maintaining it for 1-4 hrs ensured formation of a solid cross-linked resin cake from a resin solution. After crushing the cake into ~1 cm pieces of resin it was either dried in vacuum at 110-130° C. or washed repeatedly with hot (90-95° C.) water to remove ethylene glycol and than dried until water-free, milled and used for the preparation of monoliths.

In order to prepare monoliths the resin was formed into a stiff dough which was then extruded through a multi-channel die. The dough incorporated several extrusion aids in order to modify its rheological properties and enhance both the ease of extrusion and quality of the extruded monolith. These additives included grades of Methocel™, forms of poly-ethylene oxide of different chain length, poly-ethylene glycol, poly-vinyl alcohol, Revacryl™ and glycerol. The amount of water required to form the mesoporous or macroporous resin into a dough was significantly larger for the mesoporous resin due to water filling the mesopores within the resin particles and the quantities of the additives used in preparation of the dough were adjusted accordingly. The water required for the mesoporous dough was 60% of the resin weight compared to approximately 30% for a corresponding non-porous resin. Monoliths were extruded using an Instron Model 4302 universal testing machine fitted with a piston and barrel assembly to act as a ram extruder. Lengths of extruded monolith were dried on a roller table for a minimum of 24 hrs at room temperature before being cut to length and carbonised and activated at 850° C. in flowing carbon dioxide. Samples of carbonised monolith were retained for pore size and surface area analyses. Finally the monoliths were shrink-wrapped using clear heat shrink tubing (Tyco Electronics) ready for use.

Figure 3:
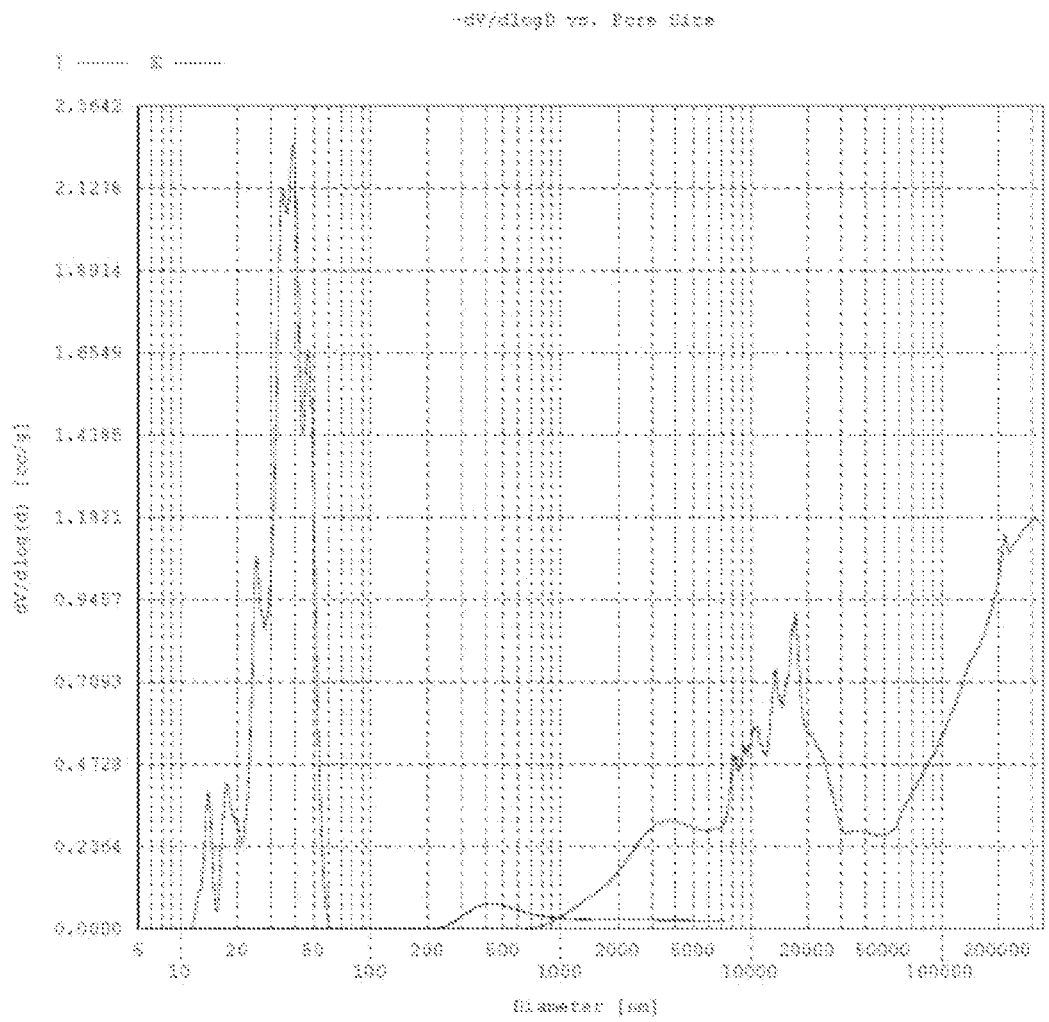
FIG. 3 is a graph of dV/d(log d) against diameter d for a carbon monolith, the data being obtained by mercury porosimetry.

A pore size distribution analysis of the sample was performed by mercury porosimetry and the result is presented on FIG. 3, which shows mesopores and macropores. In particular, FIG. 3 shows that the carbon monolith had pores in the mesopore range of 200-500 nm in size and also a larger population of macropores in the 10000-20000 nm range. Pores above 100,000 nm (100 microns) in size most likely represent channels within the monolith. The importance of the mesopores and macropores within the monolith for removal of inflammatory cytokines is considered in Example 5.

Example 5

Carbon Bead Removal of Cytokines From Human Plasma and Whole Blood

An in vitro experiment was performed to test the ability of the carbon beads, with differing pore size distribution and specific surface area (see Table 2), to adsorb inflammatory cytokines from plasma. Carbon beads (0.1 g) of Example 1-3 were weighed into Eppendorf tubes (n=3 for each of 3 incubation time points) and pre-equilibrated with phosphate buffered saline (PBS) for 2 hours in a shaking incubator at 37° C., before they were centrifuged at 8000 rpm for 5 minutes and the supernatant removed. Fresh human plasma (National Blood service) was spiked with the human recombinant inflammatory cytokines (BD Biosciences), TNF (1000 pg/ml), IL-6 (1000 pg/ml) and IL-8 (500 pg/ml). 800 µl of spiked plasma was added to each carbon bead type and incubated on a shaking incubator at 37° C. At timed intervals (30, 60 and 90 minutes) the samples were removed and centrifuged at 8000 rpm and the plasma was removed and frozen at −20° C. before analysis. Samples were analysed by enzyme linked immuno-adsorbent assay (ELISA) (BD Biosciences) and the concentrations of cytokines were calculated.

Figure 4:
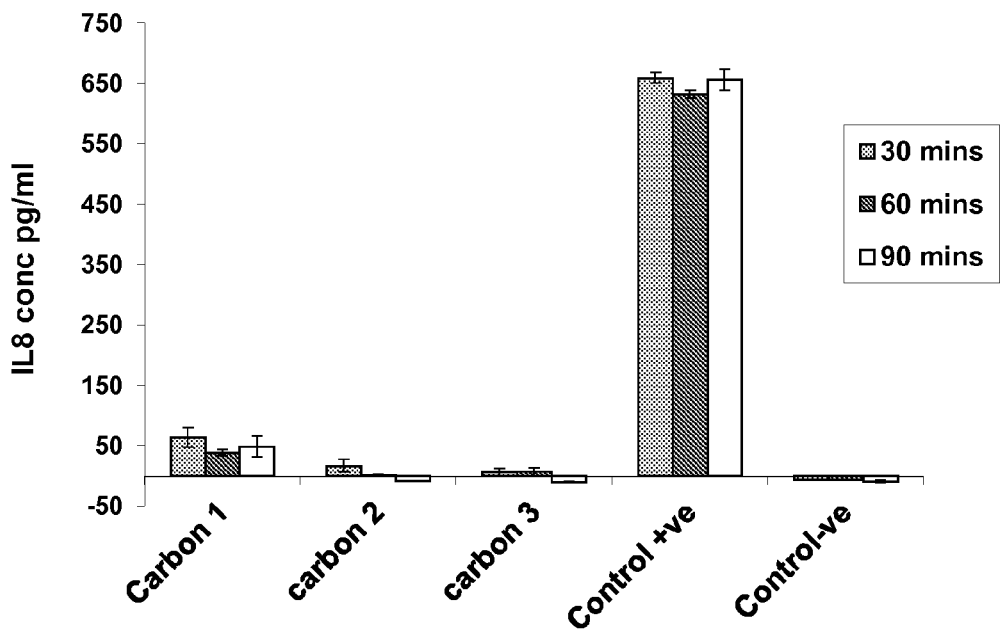
FIGS. 4-16 are bar charts, graphs and micrographs showing results obtained with carbon monoliths and carbon beads contacting human plasma and whole blood spiked with contrary substances.

FIG. 4 shows the concentration of IL-8 remaining in spiked plasma incubated with carbon 1 TE1/20 (small mesopores) and meso-macroporous carbons 2 (TE9/16) and 3 (TE7/20) over time (mean+/±SEM, n=3). All of the carbons removed significant amounts of IL-8. In particular, carbon 2 & 3 removed all detectable IL8 by the first 30 minute time point.

Figure 5:
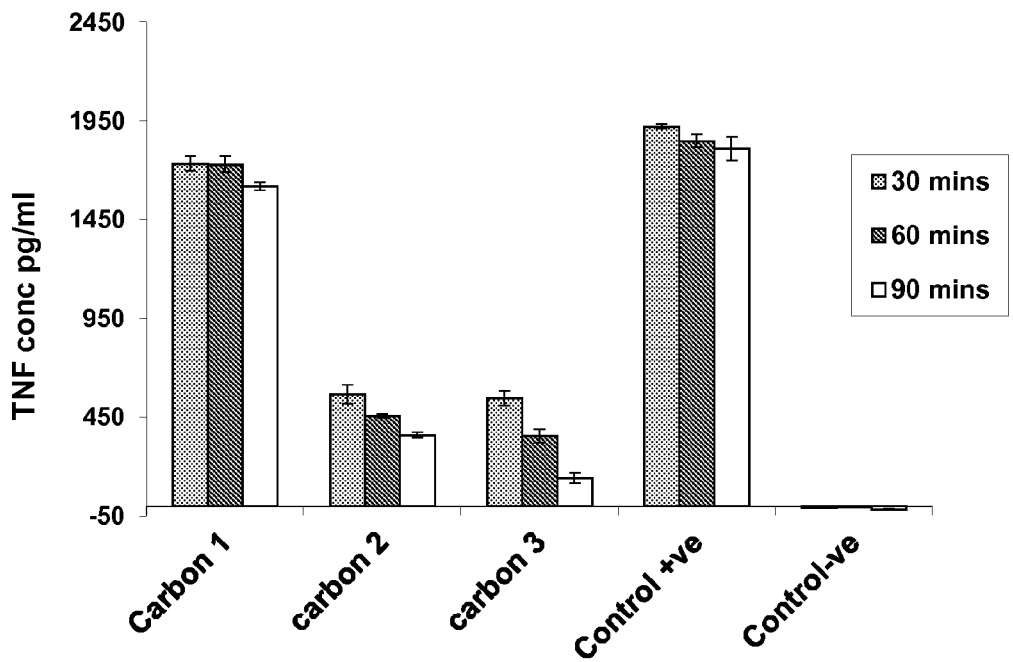

FIG. 5 shows the concentration of TNF remaining in spiked plasma incubated with the same carbon beads (mean+/−SEM, n=3). The removal of TNF by the carbon beads was restricted to carbons 2 and 3 which contain the meso-macroporous domains, The TNF molecule has a larger molecular weight than IL-8 and IL-6 and its removal is dependent on the presence of the larger meso-macropores.

Figure 6:
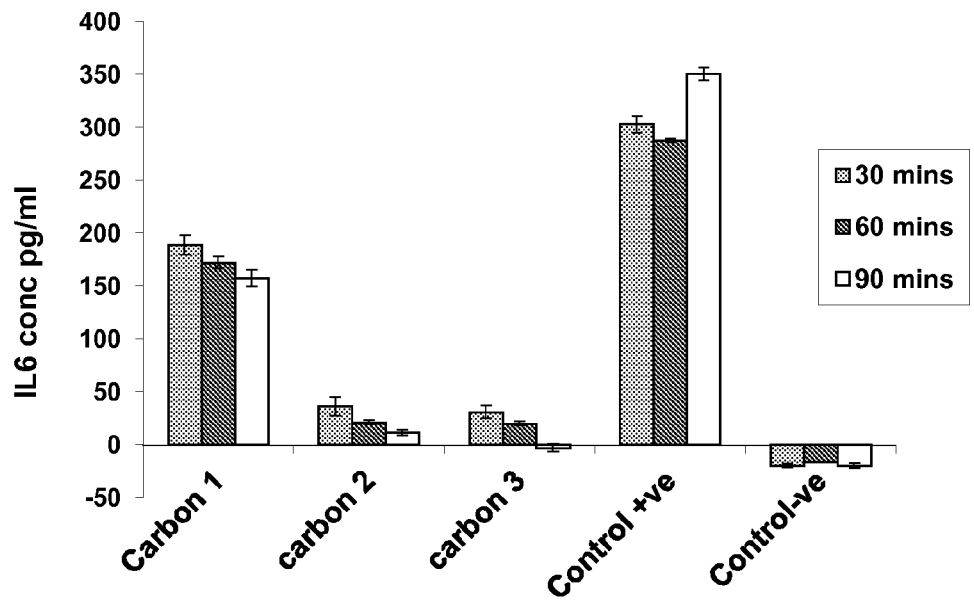

FIG. 6 shows the concentration of IL-6 remaining in spiked plasma incubated with the same carbon beads. Carbon 1, with limited mesoporosity reduced the concentration of IL-6 in the plasma by half Carbons 2 and 3 with larger mesopores removed almost all of the IL6 present.

It is believed having regard to the observed absence of haemolysis with the present carbons that the above results may be extrapolated to removal from whole blood.

Example 6

Monolith Removal of Cytokines From Blood

A continuous circuit was set up drawing fluid from a reservoir via a peristaltic pump through silicon tubing to pass through a carbon monolith made as described with reference to Example 4 and having the pore size distribution of FIG. 3 and back to the reservoir.

Monoliths of Example 4 were pre-equilibrated with phosphate buffered saline (PBS) for 20 minutes at a flow rate of 5 ml/min. Fresh frozen plasma from the NBS was defrosted, or human blood was drawn from volunteers into heparinised vacuette tubes, pooled and then the plasma or blood was spiked with the human recombinant inflammatory cytokines (BD Biosciences) TNF (500 pg/ml), IL-6 (1000 pg/ml) and IL-8 (200 pg/ml). 20 mls of the spiked plasma or blood was pumped through the monoliths at a flow rate of 5 ml/min, and 1 ml aliquots of plasma/blood were collected into eppendorf tubes at timed intervals prior to returning to the reservoir. Collected blood samples were centrifuged at 8000 rpm at 4° C. and the supernatant plasma was removed and stored at −20° C. before analysis. A set of control experiments was also conducted using un-spiked plasma or blood flowed through the monoliths and cytokine spiked plasma or blood flowed through silicon tubing only, to investigate the effect of the monolith itself on blood cell secretion of cytokines and to assess whether cytokine removal was a result of cytokine adherence to the tubing. Samples were analysed by ELISA (BD Biosciences) and the concentrations of cytokines were calculated.

Figure 7:
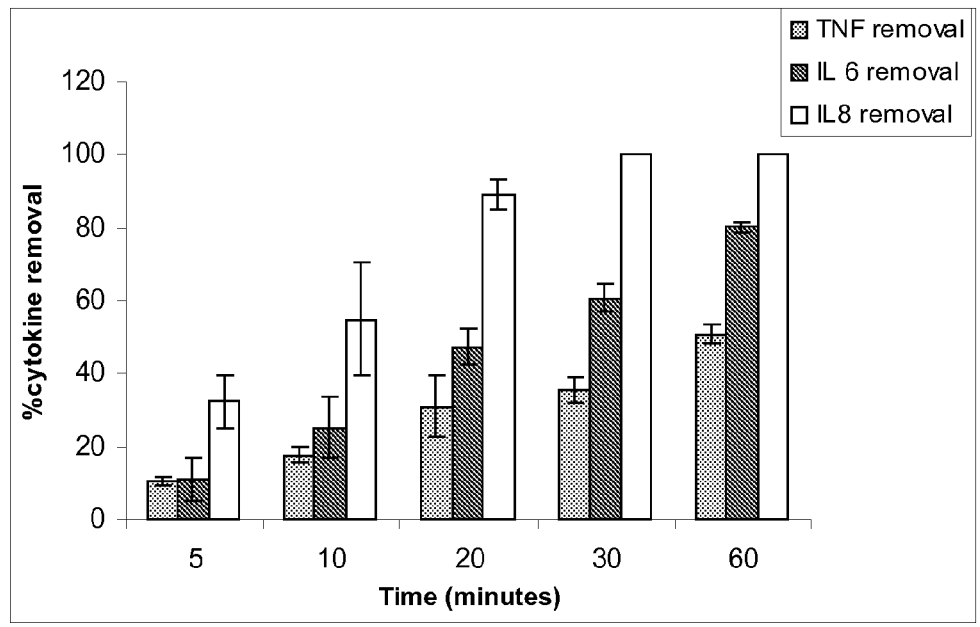

It has been found that IL-6 was well removed from plasma over time during continuous flow through the monoliths at a flow rate of 5 ml/min. FIG. 7 shows that all 3 cytokines TNF, IL-6 and IL-8 were also removed from blood over time during continuous flow through the monolith at a flow rate of 5 ml/min. The removal of TNF reached 50% over the course of the experiment and follows the pattern of removal from previous experiments concerning removal from plasma by mesoporous carbon beads disclosed in Howell C A et al., 2006 *Biomaterials* 27(30):5286-5291. TNF is a relatively large protein of 51 kDa in size, with a unit cell size of 9.4×9.4×11.7 nm, (see Reed C, Fu Z Q et at (1997) *Protein Eng* 10:1101-1107) and therefore orientation into pores is restricted by its size, Meso-macroporous domains are required for its removal.

IL-6 is a 26 kDa protein with a unit cell size 4.9×4.9×12.2 nm, (see Somers, W. Stahl, M. Seehra, J. S., *EMBO J.* v16 pp. 989-997, 1997). It is smaller in size and will orientate into both small macropores and smaller mesopores unlike TNF. This is reflected in the 80% removal observed after 60 minutes. The smallest cytokine, IL-8, is an 8 kDa protein with a unit cell size of 4×4×9 nm (Rajarathnam K, Clark-Lewis I, Sykes B D (1995) *Biochem* 34:12983-12990) and shows the greatest removal with complete removal from blood after 30 minutes circulation.

When un-spiked blood was continuously passed through the monolith no cytokine production was observed over the time course of the experiment, indicating that the monolith induced no further cytokine production by activation of inflammatory cells.

Example 7

Figure 8:
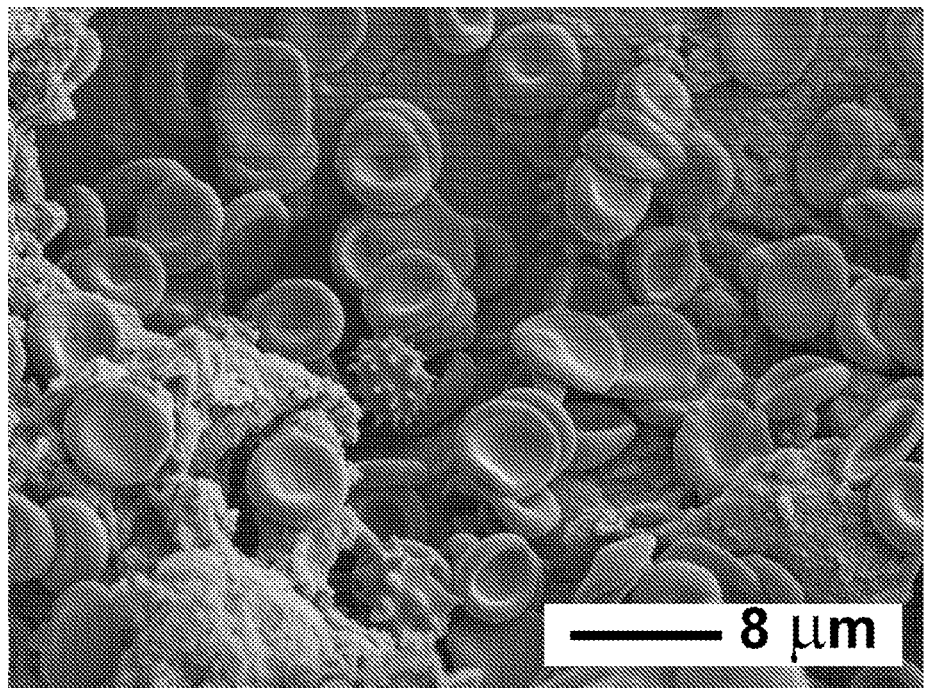

Granulocyte Activation During Continuous Circulation Through Carbon Monolith Channels Human neutrophil elastase (HNE) is secreted by granulocytes during inflammation. It forms a subfamily of serine proteases that hydrolyze many proteins in addition to elastin and can destroy bacteria and host tissue. Blood samples collected following circulation through a monolith made as described in Example 4 were analysed for free and bound natural HNE in plasma by ELISA (Cambridge Bioscience). Monoliths were examined for cell adhesion by scanning electron microscopy (SEM). Samples were washed in PBS then fixed in glutaraldehyde before dehydration in a series of ethanol solutions. Samples were mounted onto aluminium stubs, sputter coated with palladium using a positron SC7640 sputter coater and viewed using a Jeol JSM-6310 SEM set at 10 kV. Results shown in FIG. 8 which is an SEM image of the internal surface of a monolith produced according to the method described in Example 4, after passage of unspiked blood, showing erythrocytes and leukocytes adhering to the walls of the monolith. The images show that inflammatory white blood cells while they have adhered to the monolith surface, they have not spread out and become activated. The erythrocytes are also in good conformation and have not been haemolysed by contact with the surface of the monolith.

Figure 9:
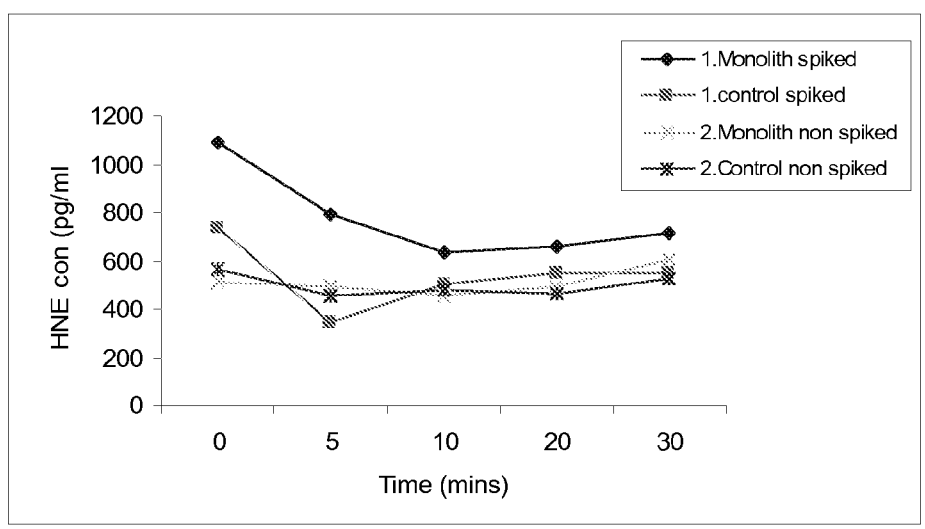

A higher level of elastase was measured in samples collected from cytokine spiked blood passed through the monolith (labelled monolith spiked) than in samples of spiked and un-spiked blood not circulated through the monoliths (labelled control spiked/non spiked) or in un-spiked blood passed through the monoliths (labelled monolith non spiked) (FIG. 9). Results show that, as expected, spiking blood with cytokines activated granulocytes caused them to secrete FINE. Blood that was not spiked with cytokine and was then passed through the monolith produced similar FINE levels to those of the unfiltered, un-spiked control. The results therefore suggest that the cytokines added to the blood induce neutrophil activation not the monolith itself.

Example 8

Haemolysis of Blood During Continuous Circulation Through the Carbon Monolith Channels Blood samples collected after circulation through the monoliths of Example 4 were used to determine haemolysis. Samples were collected at the start and end of blood circulation through the monoliths. 20 μL aliquots of cytokine spiked and un-spiked blood were collected, diluted in PBS and centrifuged at 1000 g for 15 minutes. The control, showing full haemolysis, was prepared by diluting a blood sample in water. The absorbance of the supernatant was measured on a spectrophotometer at 405 nm, zeroed for PBS. The absorbance values indicate that there is a small degree of haemolysis experienced in the spiked blood that has passed through the monoliths, in comparison to no haemolysis measured for the un-spiked blood.

Measurement of hemolysis of blood is a standard practice for extracorporeal devices. There is always a certain degree of hemolysis to blood caused by the collection procedure from a volunteer, but other factors such as surface roughness of the device can cause further hemolysis. The levels of hemolysis that were measured for the monoliths was only slightly increased in the case of the spiked cytokine-containing blood on passage through the monolith. The increased levels of inflammatory cytokines may have influenced the degree of hemolysis, because in the case of the un-spiked blood there was no increase in hemolysis measured after passage through the monolith. The results indicate that the monolith is not causing blood cell hemolysis upon circulation through the monolith and is therefore suitable as a device for extracorporeal applications.

TABLE 2

Measurement of haemolysis for cytokine spiked and un-spiked blood flow through monolith with absorbance measured at 405 nm.

| Time | Spiked blood through monolith | Un-spiked blood through monolith | Total haemolysis |
|---|---|---|---|
| Monolith start | 0.0086 | 0 | 2.158 |
| 60 mins | 0.0204 | 0 | |

Example 9

Removal of Superantigen Bacterial Toxin SEA and SEB From Plasma and Whole Blood by Carbon Beads A number of experiments were performed to test the ability of the carbon beads to adsorb bacterial superantigens in vitro from plasma. Batch adsorption experiments were conducted using 0.1 g samples of various carbon beads incubated with spiked plasma over time. Fresh frozen human plasma (NBS) was spiked with the exotoxin Staphylococcal enterotoxin A (SEA) or Staphylococcal enterotoxin (SEB) (Toxin Technology) at a concentration of 100 ng/ml. Carbon samples and controls were pre-incubated with PBS overnight in a shaking incubator at 37° C. Samples were centrifuged at 8000 rpm and the supernatant removed prior to addition of 800 μL of the spiked plasma and incubation in the shaking incubator at 37° C. At timed intervals the samples were removed and centrifuged at 8000 rpm and frozen at −20° C. before analysis. Samples were analysed by ELISA using a set of paired antibodies (Toxin Technology) and the concentration of SEA or SEB was calculated. The example was repeated exotoxin toxic shock syndrome toxin 1 (TSST-1) in PBS (data not shown).

Figure 10:
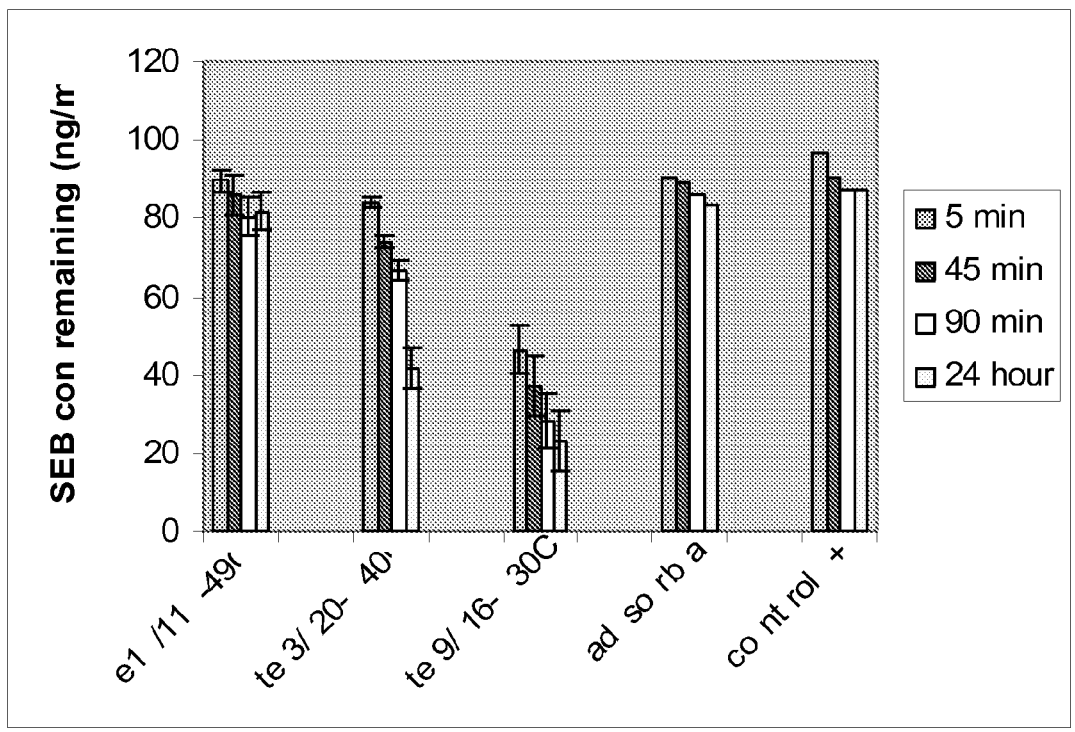
Figure 11:
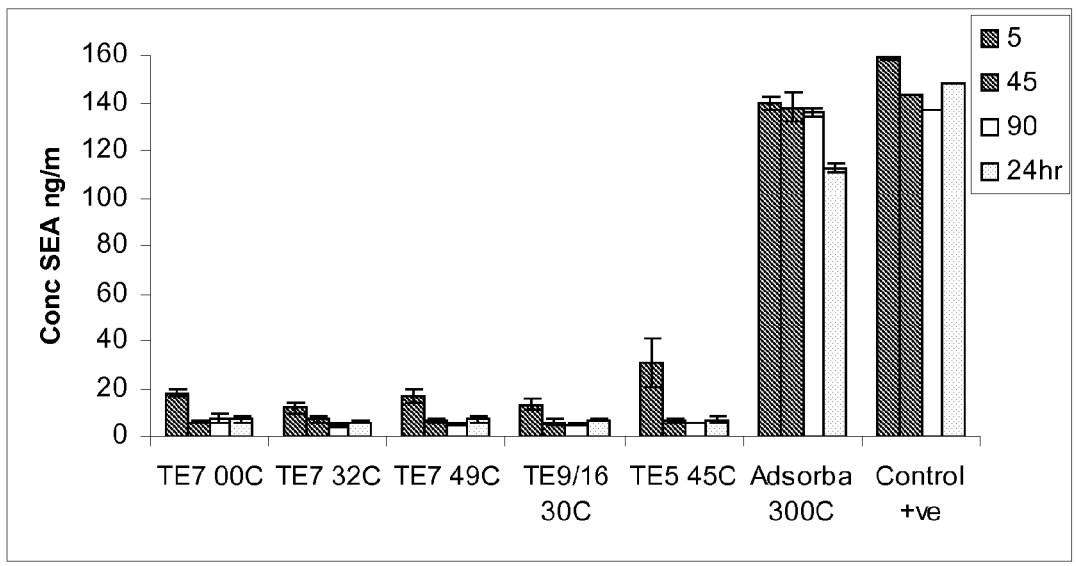
Figure 12:
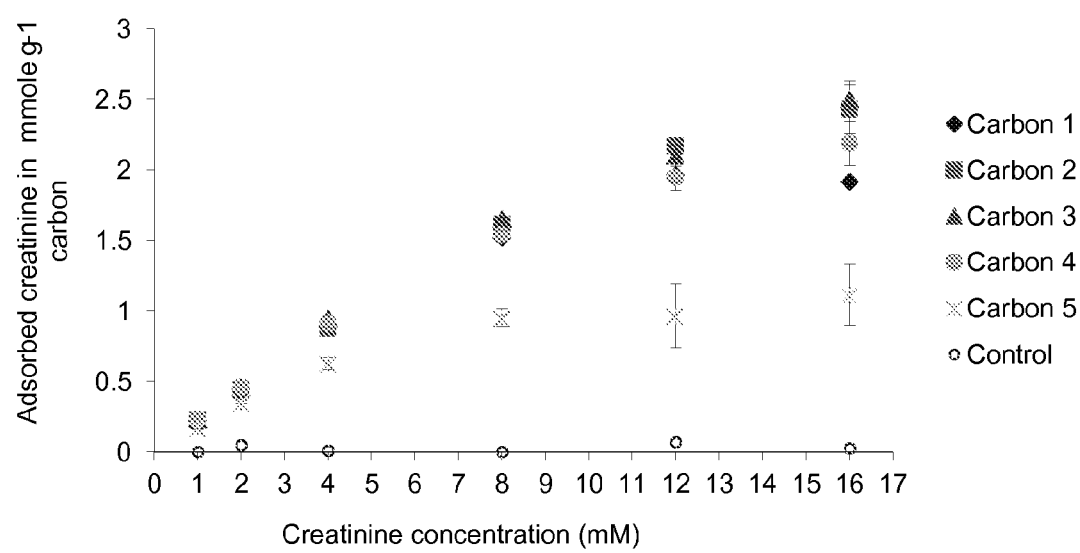

FIG. 10 shows the concentration of SEB remaining in spiked plasma incubated with microporous e1/11-22c (low activation), mesoporous te3/20-22c (moderately activated) and meso-macroporous te9/16-30c (highly activated) carbon over time, n=3, mean+/−SEM). SEB was not removed by the purely microporous e1 carbon but was removed by up to 50% by te9 the meso-macroporous carbon bead. FIG. 12 shows significant removal of the toxin SEA from plasma by meso-macroporous carbon te7 in 3 different activation degrees 00 C, 32 C and 49 C.—made with 250 parts ethylene glycol per 100 parts resin (TE7). Similarly the large mesoporous (TE5) and meso-macroporous carbon (TE9) showed good removal of SEA from plasma over time. In particular, FIG. 11 shows concentration of SEA remaining in plasma incubated with mesoporous carbon beads produced according to the method described in Example 1-3, and commercial control Adsorba 300C (n=3, mean+/−SEM). It is believed that the results reported therein can be extrapolated to the extracorporeal treatment of whole blood.

Example 10

Mast Carbon Bead Removal of Creatinine From Human Plasma and Whole Blood

A batch experiment was performed to show the adsorption capacity of mesoporous/microporous or macroporous/microporous carbons beads—E1/11 TE-7/20, TE-3/20 and TE 9-16 (for preparative details see preceding examples) for creatinine. 15 mg samples of each carbon were equilibrated in 4 ml Tyrode's buffer (137 mM NaCl, 2.8 mM KCl, 12 mM NaHCO$_3$, 5.5 mM glucose, 0.4 mM NaH$_2$PO$_4$ and 10 mM Hepes, pH7.4) overnight at 25° C. The Tyrode's buffer was then removed and 5 ml of different concentrations of creatinine in Tyrode's buffer were added to each carbon (0.5 mM, 1 mM, 2 mM, 4 mM, 8 mM, 12 mM, 16 mM). The samples were incubated shaking for 24 hours at 37° C. Samples were measured with a UV-spectrophotometer, and concentrations of creatinine remaining in the solution calculated from the standard curve. All the activated carbons studied possessed the ability to adsorb creatinine from solution (see FIG. 12 which is an adsorption isotherm for creatinine adsorption by carbon 1 (TE7/20-43), carbon 2 (TE3/20-40C), carbon 3 (TE9/16-30C) produced according to the method described in Example 1-3 and commercial control Adsorba 300 C (n=3, mean+/−SEM)). Uremic patient levels can rise to 1.2 mM and the experimental results indicate that Mast carbons, with a capacity to remove 2.5 mmoles g$^{-1}$ of carbon, could remove clinically significant levels of creatinine in an adsorbent system. It is believed having regard to the observed absence of haemolysis with the present carbons that the above results may be extrapolated to whole blood.

Example 11

Mast Carbon Bead Removal of Uremic Toxins P-Cresyl Sulphate and Indoxyl Sulphate From Human Plasma and Whole Blood Human plasma was spiked with indoxyl sulphate (IS) (125 μM), p-cresyl sulphate (PCS) (250 μM) and IL-6 (1000 pg ml$^{-1}$). 0.1 g of each carbon sample was weighed into an eppendorf 1.5 ml tube and pre-equilibrated with PBS for 1 hour at 37° C. A commercial microporous only control Adsorba 300 C was also tested. Samples were centrifuged, the PBS was removed and 0.8 ml of spiked plasma was added to each tube. Samples were placed on a shaking incubator at 37° C. and samples were taken at 5, 15, 30 and 60 minute time points. Plasma samples were analysed for PCS and IS content using high performance liquid chromatography (HPLC).

TABLE 3

Carbon bead pore data used for IS and PCS removal studies

| Sample | Bead Diameter (μm) | Surface Area S$_{BET}$ (m$^2$g$^{-1}$) | Pore Volume (cm$^3$g$^{-1}$) | Bulk Density (gcm$^{-3}$) | Mean mesopore diameter (nm) |
|---|---|---|---|---|---|
| Carbon 1 (te5) | 250-500 | 1493 | 1.75 | 0.27 | 70 |
| Carbon 2 (te7) | 250-500 | 1483 | 2.11 | 0.21 | 80 |
| Carbon 3 (te9) | 250-500 | 1236 | 1.61 | 0.18 | 120 |
| Carbon 4 (te3) | 250-500 | 1465 | 1.30 | 0.38 | 30 |

Figure 13A:
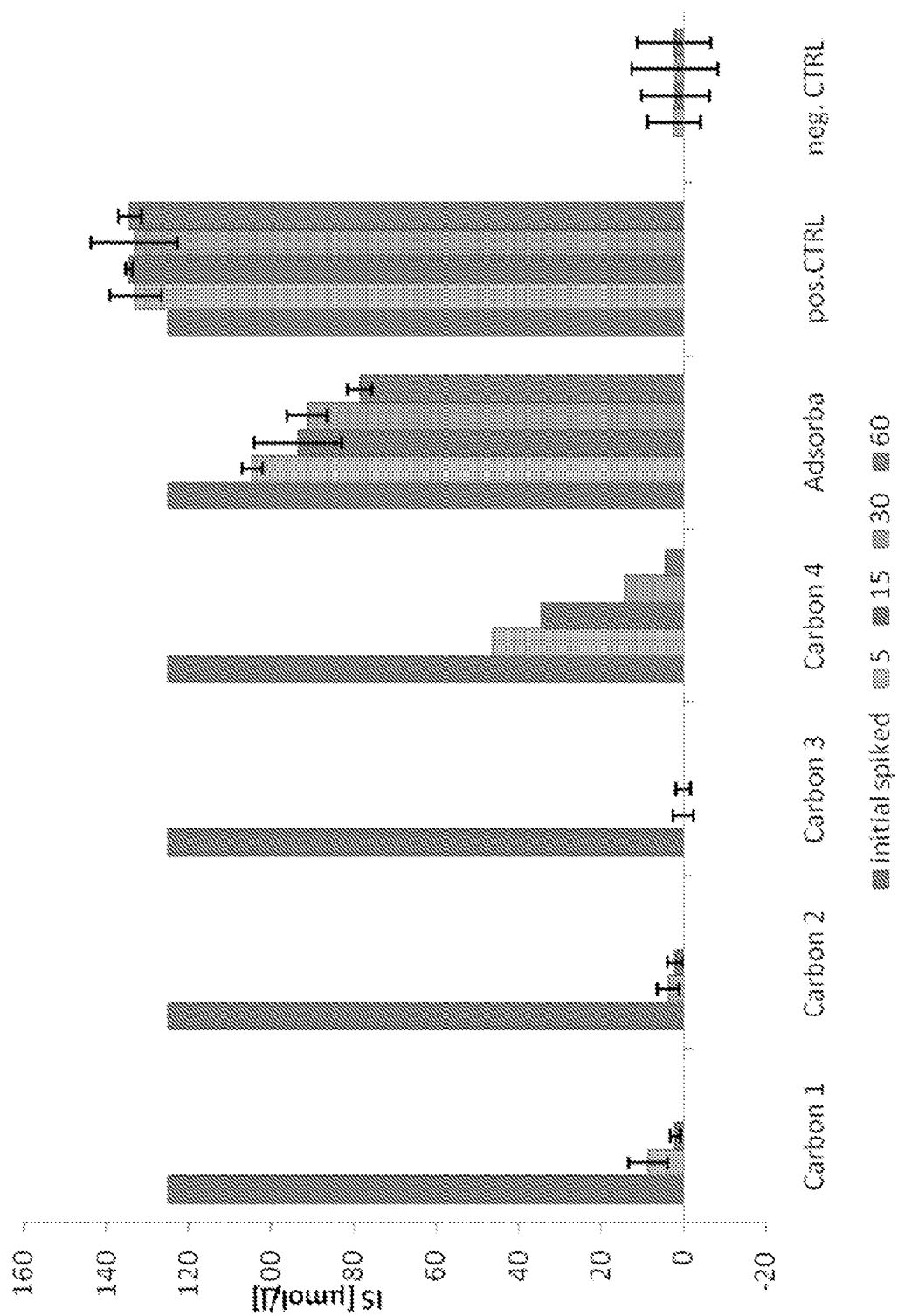
Figure 13B:
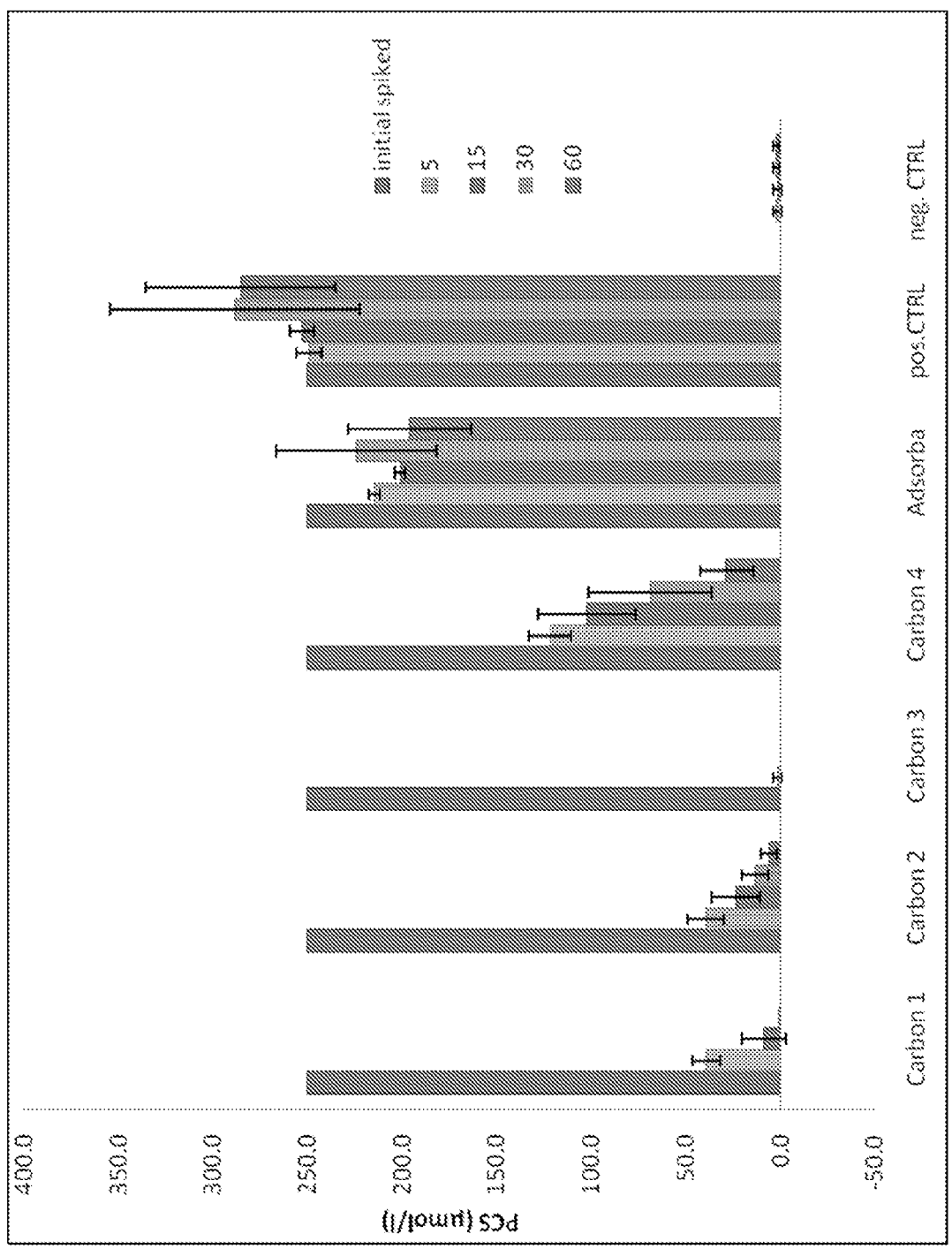

FIGS. 13a and 13b show removal of uremic toxins a. indoxyl sulphate and b. p-cresyl sulphate from human plasma by carbon beads 1 to 4 produced according to the method described in Example 1-3 and commercial control Adsorba 300C (n=3, mean+/−SEM). It is believed having regard to the observed absence of haemolysis with the present carbons that the above results may be extrapolated to whole blood.

Example 12

Figure 14A:
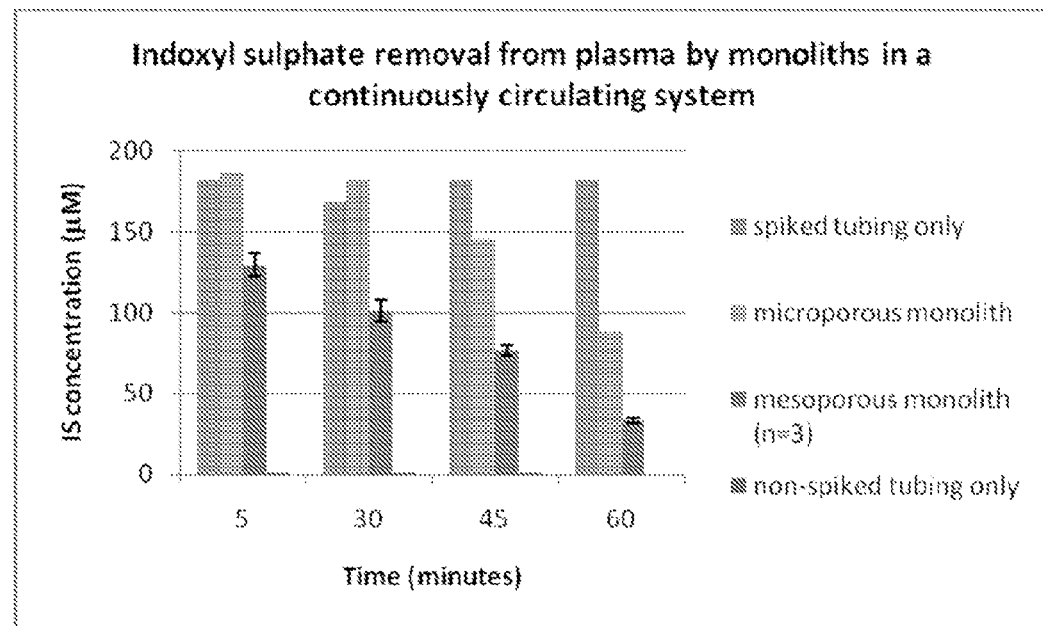
Figure 14B:
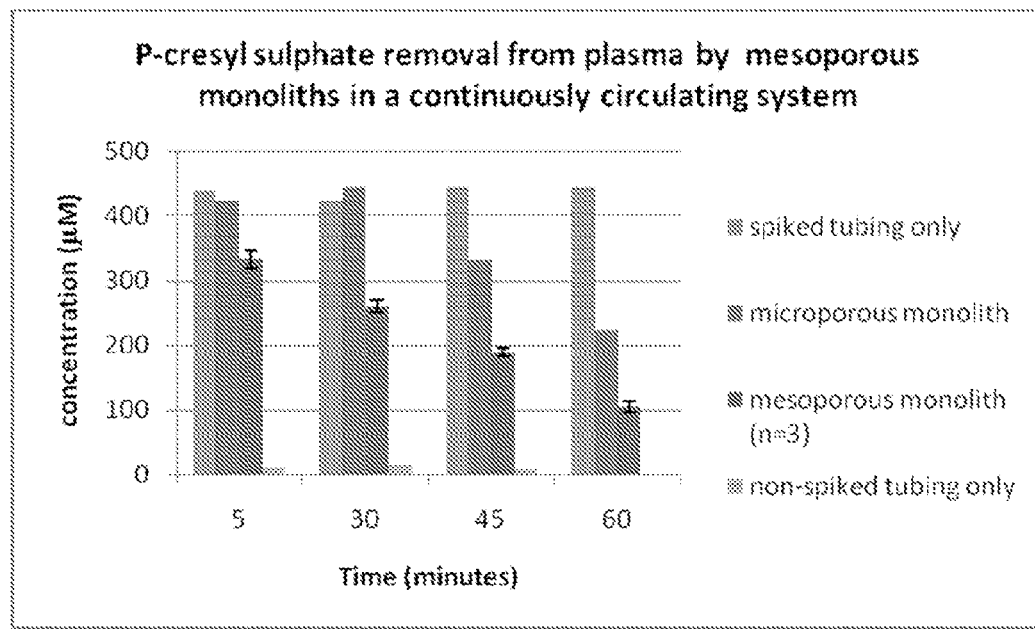
Figure 15:
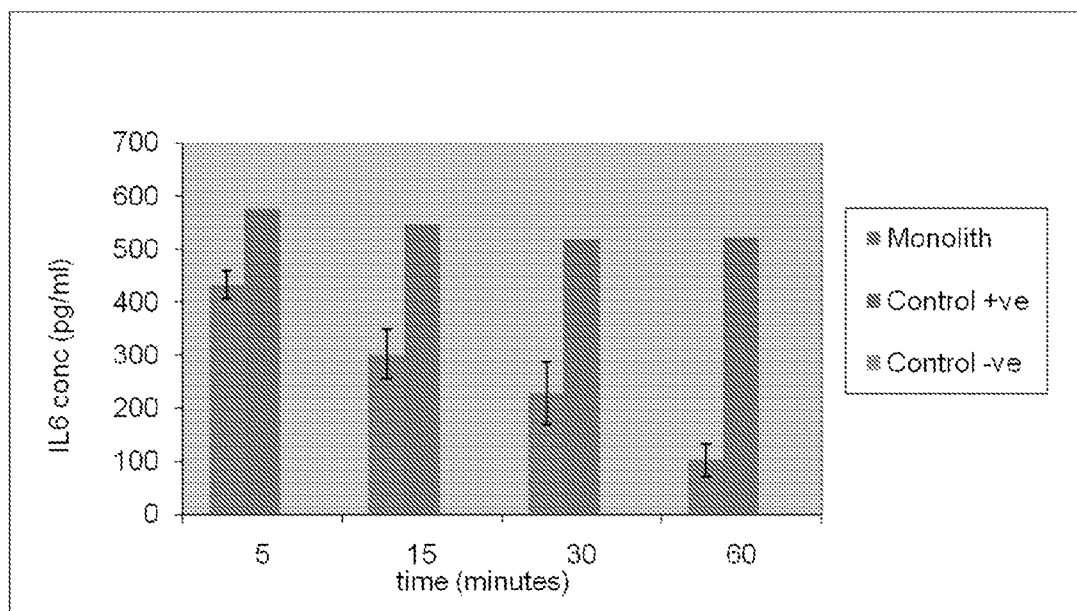

Measuring the Removal of Uremic Toxins P-Cresyl Sulphate and Indoxyl Sulphate from Human Plasma and Whole Blood by Mast Carbon Monoliths Human plasma was spiked with indoxyl sulphate (IS) (125 μM), p-cresyl sulphate (PCS) (250 μM) and IL-6 (1000 pg ml$^{-1}$). The carbon monoliths tested were mesoporous monoliths made from TE7-20 cake and a microporous monolith control made from microporous resin only. The monoliths were connected, via tubing, to a multiple channel peristaltic pump and a reservoir containing the spiked plasma. The monoliths were pre-equilibrated with PBS and drained. The spiked plasma was then passed through the monoliths at a flow rate of 5 ml per minute and plasma samples were collected at specific time points. Cytokine removal was measured by ELISA. Indoxyl sulphate and p-cresyl sulphate removal was measured by high performance liquid chromatography (HPLC). The mesoporous monoliths removed the uremic toxins indoxyl sulphate and p-cresyl sulphate and the cytokine IL-6 (FIGS. 14a,14b & 15). FIGS. 15a and 15b show removal of uremic toxins a. indoxyl sulphate and b. p-cresyl sulphate from human plasma by carbon monoliths produced according to the method described in Example 4 in a continuously circulating system (n=3, mean+/−SEM). FIG. 15 shows removal of cytokine IL6 by Mast carbon monoliths produced according to the method described in Example 4 in a continuously circulating system (n=3, mean+/−SEM). Monolith filtration reduced IS concentration to one sixth of the original spiked concentration and PCS concentration to one quarter the original spiked concentration over the 60 minute filtration time. Some reduction in PCS and IS levels occurred on filtration through the microporous monolith. It is believed having regard to the observed absence of haemolysis with the present carbons that the above results may be extrapolated to whole blood.

Example 13

Measuring the Removal of Liver Toxins by Mast Carbon Beads of Varying Pore Size Distribution Mast carbon beads with varying micro, meso and macroporous domains were used to assess removal of small and protein bound biological molecules relevant to liver failure. The carbon adsorbents were washed three times using 0.9% NaCl solution before each batch test. 0.6 mL of wet adsorbents was transferred to a fresh 15 mL centrifuge tube. Human plasma was spiked with 300 μM bilirubin, 100 μM cholic acid, 100 μM tryptophan and 2 mM phenol. 5.4 mL of spiked plasma was added to each tube of carbon adsorbent. The mixtures were then incubated in a rotating oven at 37° C. for 5 min, 15 min, 30 min and 60 min. One mL of adsorbent/plasma mixture was taken from the tube at each time point. The adsorbent/plasma mixtures were then centrifuged, and the supernatants were transferred into eppendorf tubes with 400 μL aliquots. The samples were all kept in −20° C. freezer prior to HPLC and Hitachi analysis.

Figure 16A:
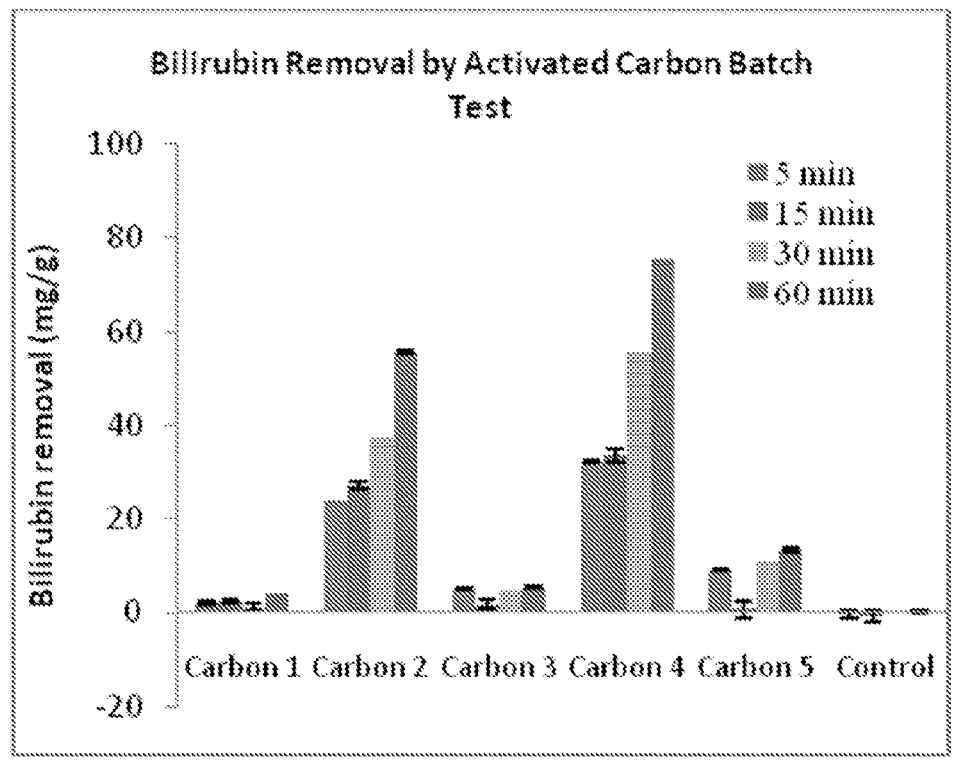

All of the carbon beads removed the small molecular weight molecules cholic acid, tryptophan and phenol (data not shown). However, only the carbons with larger meso-macroporous domains were able to remove the albumin bound liver toxin bilirubin. The removal of bilirubin and albumin followed the same pattern suggesting that bilirubin is removed as a protein bound molecule (FIG. 16a, b).

TABLE 4

Carbon beads used to assess removal of small and protein bound biological molecules relevant to liver failure.

| | Mean mesopore diameter (nM) | Specific surface area (sq · m/g) |
|---|---|---|
| Carbon 1 | — | 1204 |
| Carbon 2 | 80 | 1548 |
| Carbon 3 | 30 | 1559 |
| Carbon 4 | 120 | 1235 |
| Carbon 5 | 70 | 1493 |

Figure 16B:
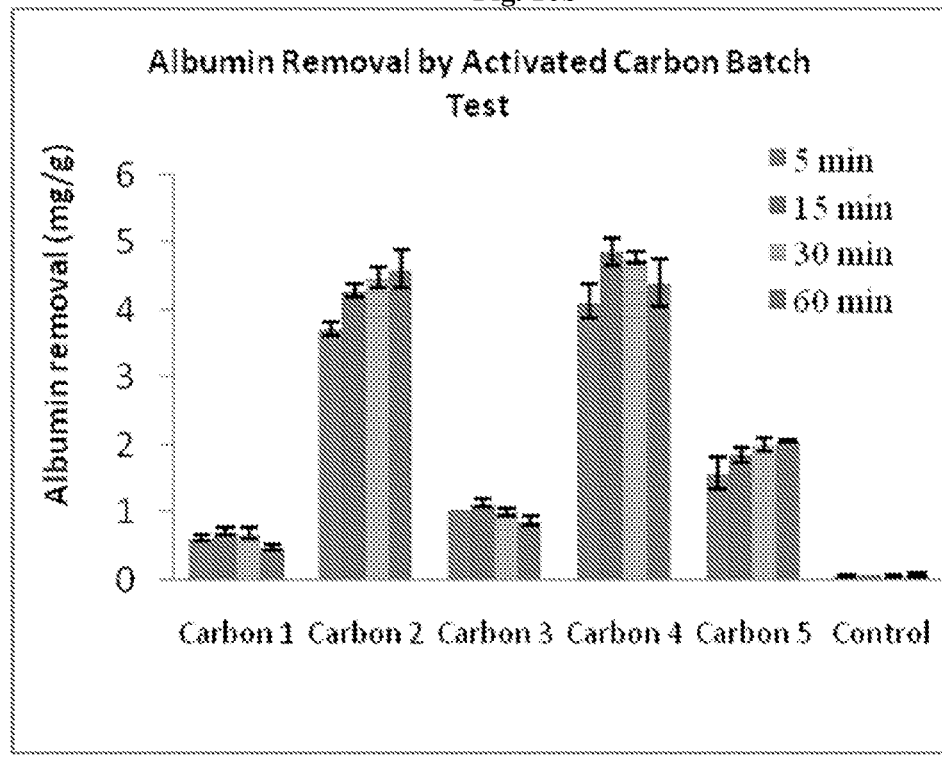

FIG. 16a shows removal of liver toxin bilirubin by carbon beads in mg per gram of carbon. Carbon 1 (E1), 2(te7), 3(te3), 4(te9), 5(te5) are carbon beads with different pore size distribution produced according to the method described in Example 1-3 (n=3, mean+/−SEM) FIG. 16b shows removal of albumin by Mast carbon beads in mg per gram of carbon (n=3, mean+/−SEM). It is believed having regard to the observed absence of haemolysis with the present carbons that the above results may be extrapolated to whole blood.

The invention claimed is:

1. A method for extracorporeal treatment of whole blood to remove a contrary substance therein and provide treated blood returnable to the body, which method comprises contacting the whole blood with a material consisting of uncoated microporous/mesoporous or microporous/macroporous carbon wherein the whole blood is not separated into cells and plasma.

2. The method of claim 1, wherein the contrary substance is ADMA, creatinine, or another low molecular weight water-soluble molecule.

3. The method of claim 1, wherein the contrary substance is a p-cresyl sulphate, indoxyl sulphate or another protein bound solute.

4. The method of claim 1, wherein the contrary substance is a staphylococcus enterotoxin B (SEB), SEA or a bacterial toxin.

5. The method of claim 1, wherein the contrary substance is a lipopolysaccharide.

6. The method of claim 1, wherein the contrary substance is a cytokine.

7. The method of claim 1, wherein the contrary substance is selected from IL-1β, IL-4, IL-6, IL-8, IL-10, IL-11, IL-13 and TNF.

8. The method of claim 1, wherein the contrary substance is a small or protein bound biological molecule.

9. The method of claim 8, wherein the molecule is bilirubin, cholic acid, tryptophan or phenol.

10. The method of claim 1, wherein the carbon has a pore size distribution showing a first large population of micropores of size<2 nm and a second large population of macropores of size 50-500 nm.

11. The method of claim 10, wherein the carbon further comprises mesopores of size 2-50 nm.

12. The method of claim 1, in which the monolith has a surface area of 800-1500 m²/g.

13. The method of claim 1, wherein the carbon is from carbonization and activation of a mesoporous or macroporous phenolic resin.

14. The method of claim 1, wherein the carbon is in the form of beads.

15. The method of claim 1, wherein the carbon is in the form of a monolithic porous carbon structure.

16. The method of claim 15, wherein the monolithic porous carbon structure has
(i) continuous channels through which blood can pass with a channel size of between 200 and 1000 μm;
(ii) wall thickness between 200 and 1000 μm;
(iii) macropores within the walls with a mean pore size of between 1 and 50 μm; and
(iv) pores within the carbon matrix suitable for the adsorption of middle and high molecular weight molecules with a mean pore size between 2 and 500 nm.

17. The method of claim 15, wherein the monolithic porous carbon structure is the result of:
partially curing a phenolic resin plus a pore former to a solid;
comminuting the partially cured resin;
removing the pore former by either washing or vacuum drying;
milling the comminuted resin to a particle size from 10 to 100 microns;
extruding the milled resin;
sintering the extruded resin so as to produce a form-stable sintered product; and
carbonising and activating the form-stable sintered product.

18. The method of claim 17, wherein the particles of the milled resin are of size 1-250 μm.

19. The method of claim 18, wherein the particles of the first resin are of size 10-70 μm.

20. The method of claim 17, wherein the particles of the first resin are of size 20-50 μm.

21. The method of claim 17, wherein the particles of the resin are the result of comminuting followed by jet milling.

22. The method of claim 17, wherein the first phenolic resin is a hexamine-cured novolac resin.

23. The method of claim 17, which comprises forming a dough by mixing the resin particles with methyl cellulose, PEO and water.

24. The method of claim 23, wherein the dough is extruded to form a shaped body having walls defining a multiplicity of internal channels for fluid flow, the channels being directed along the extrusion direction.

25. The method of claim 1, wherein the blood is from a patient suffering from sepsis or systemic inflammatory response syndrome (SIRS) consisting of an excess of cytokines, where an incoming stream being removed from the patient is cleansed of cytokines and bacterial toxins and an output stream of the treated blood being for return to the bloodstream of the patient.

26. The method of claim 1, wherein the blood is from a patient with end-stage renal failure who is receiving hemodialysis (HD), that does not remove protein bound and larger molecular weight uremic toxins which remain in the body.

27. The method of claim 1, wherein the blood is from a patient with liver failure.

* * * * *